US011793426B2

(12) United States Patent
Parchani et al.

(10) Patent No.: US 11,793,426 B2
(45) Date of Patent: Oct. 24, 2023

(54) SYSTEM AND A METHOD FOR DETERMINING BREATHING RATE AS A BIOFEEDBACK

(71) Applicant: Turtle Shell Technologies Private Limited, Bengaluru (IN)

(72) Inventors: Gaurav Parchani, Bengaluru (IN); Mudit Dandwate, Bengaluru (IN)

(73) Assignee: Turtle Shell Technologies Private Limited

( * ) Notice: Subject to any disclaimer, the term of this patent is extended or adjusted under 35 U.S.C. 154(b) by 377 days.

(21) Appl. No.: 17/003,213

(22) Filed: Aug. 26, 2020

(65) Prior Publication Data
US 2021/0059539 A1    Mar. 4, 2021

(30) Foreign Application Priority Data

Aug. 27, 2019 (IN) .............................. 201941034439

(51) Int. Cl.
*A61B 5/113* (2006.01)
*A61B 5/0205* (2006.01)
(Continued)

(52) U.S. Cl.
CPC ............ *A61B 5/113* (2013.01); *A61B 5/0205* (2013.01); *A61B 5/02405* (2013.01);
(Continued)

(58) Field of Classification Search
CPC ... A61B 5/0205; A61B 5/02405; A61B 5/113; A61B 5/486; A61B 5/7246;
(Continued)

(56) References Cited

U.S. PATENT DOCUMENTS

2006/0241510 A1* 10/2006 Halperin .............. A61B 5/6892
600/534
2009/0203972 A1* 8/2009 Heneghan .............. G16H 40/63
600/301
(Continued)

FOREIGN PATENT DOCUMENTS

CN          107569226 A     1/2018
TW          M575558 U       3/2019
(Continued)

OTHER PUBLICATIONS

Sharma, Nandita, and Tom Gedeon. "Objective measures, sensors and computational techniques for stress recognition and classification: A survey." Computer methods and programs in biomedicine 108.3 (2012): 1287-1301. (Year: 2012).*

(Continued)

*Primary Examiner* — David J. McCrosky
*Assistant Examiner* — Nidhi N Patel
(74) *Attorney, Agent, or Firm* — Lerner David LLP

(57) ABSTRACT

System and method for determining breathing rate as biofeedback is provided. First biomarker, second biomarker, third biomarker and fourth biomarker is extracted by computation engine from physiological parameters associated with subject by applying pre-defined set of rules. A first value is computed by feedback unit as a function of second biomarker, third biomarker and fourth biomarker. A correlation between first value and time domain parameter of fourth biomarker and frequency domain parameter of fourth biomarker is determined. First value indicates stress level of subject. Second value is computed by maximizing time domain parameter of fourth biomarker and minimizing frequency domain parameter of fourth biomarker based on correlation. Second value indicates reduced stress level of subject. Biofeedback is transmitted by feedback unit to cue generation unit which represents quantified data determined (Continued)

based on second value. The quantified data is indicative of modified second biomarker.

42 Claims, 19 Drawing Sheets

(51) Int. Cl.
  *A61B 5/00* (2006.01)
  *A61B 5/024* (2006.01)
  *G06F 18/23* (2023.01)
  *A61B 5/16* (2006.01)

(52) U.S. Cl.
  CPC ............ *A61B 5/486* (2013.01); *A61B 5/7246* (2013.01); *A61B 5/7257* (2013.01); *A61B 5/742* (2013.01); *A61B 5/7405* (2013.01); *A61B 5/7455* (2013.01); *G06F 18/23* (2023.01); *A61B 5/165* (2013.01)

(58) Field of Classification Search
  CPC ..... A61B 5/7257; A61B 5/7405; A61B 5/742; A61B 5/7455; A61B 5/165; A61B 5/6892; A61B 5/6891; A61B 5/0816; A61B 5/1102; G06K 9/6218; G06K 9/00523; G06K 9/00536
  See application file for complete search history.

(56) References Cited

U.S. PATENT DOCUMENTS

| | | |
|---|---|---|
| 2014/0163343 A1 | 6/2014 | Heneghan et al. |
| 2019/0254590 A1 | 8/2019 | Venkatraman et al. |

FOREIGN PATENT DOCUMENTS

| | | |
|---|---|---|
| WO | 2011045709 A1 | 4/2011 |
| WO | 2019000073 A1 | 1/2019 |
| WO | 2019055414 A2 | 3/2019 |

OTHER PUBLICATIONS

Parikh, Parth. Bio-Feedback Device for Meditation. Diss. California State University, Northridge, 2018 (Year: 2018).*

Paalasmaa J, Ranta M. Detecting heartbeats in the ballistocardiogram with clustering. InProceedings of the ICML/UAI/COLT 2008 workshop on machine learning for health-care applications, Helsinki, Finland Jul. 9, 2008 (vol. 9).

Meriheinä, Ulf "BCG Measurements in Beds" Murata Eelctronics Oy, Doc. No. 3875, Rev. 1, Jan. 1, 2008; 16 pages.

* cited by examiner

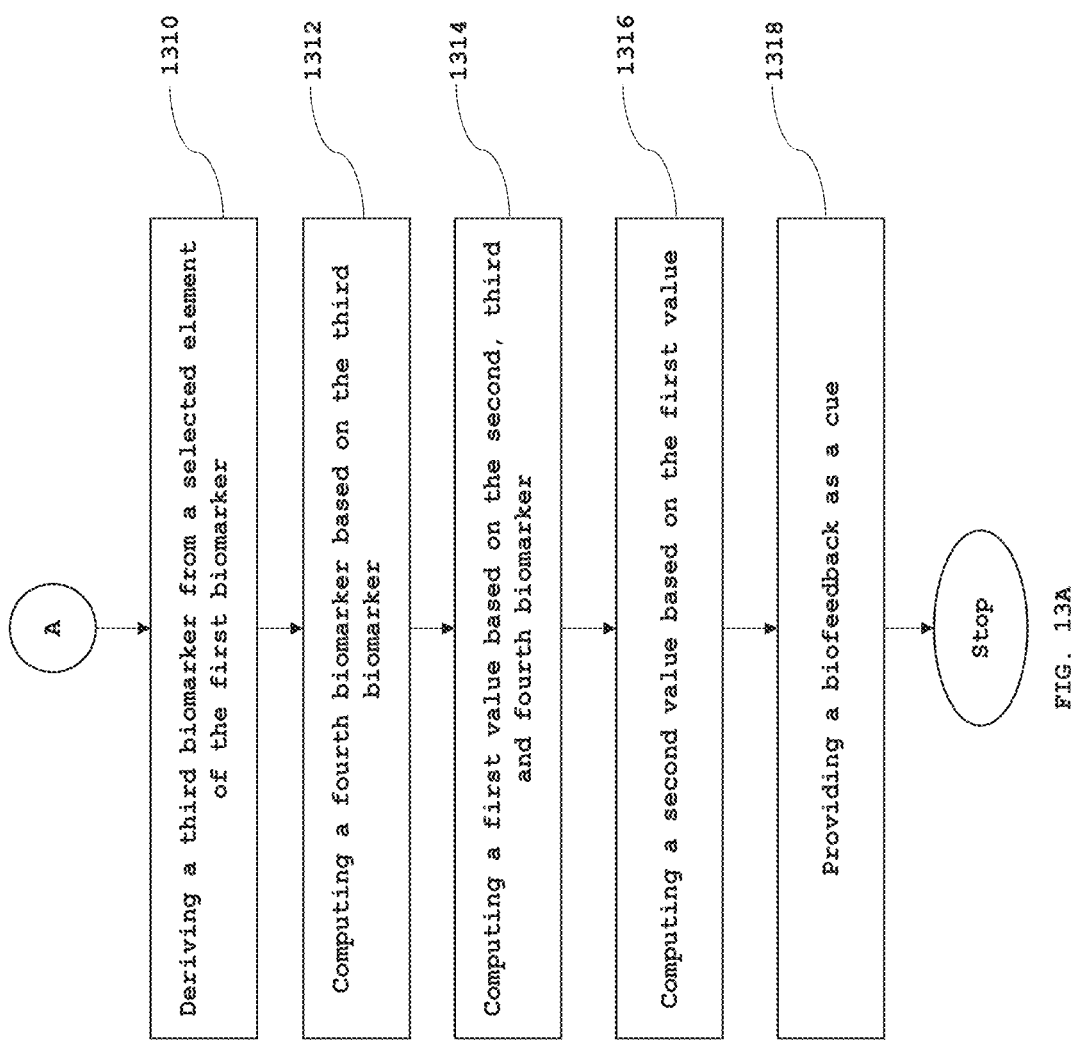

SYSTEM AND A METHOD FOR DETERMINING BREATHING RATE AS A BIOFEEDBACK

FIELD OF THE INVENTION

The present invention relates generally to the field of monitoring and analyzing physiological parameters. More particularly, the present invention relates to a system and a method for contactless detection and monitoring of physiological parameters and determining breathing rate as a biofeedback during a meditation session or an exercise session.

BACKGROUND OF THE INVENTION

In today's day and age of fast moving and stressful lifestyle, people around the world suffer from serious health related issues. Various studies have shown that people worldwide suffer from multiple health related issues out of which chronic stress and hypertension are considered the most prevalent. Hypertension may further cause severe health related issues such as, but not limited to, stroke, high blood pressure, heart failure, diabetes, kidney disease, coronary artery disease etc. Further, chronic stress and hypertension, if left unattended, can cause complex and fatal health disorders such as cardiovascular diseases, chronic obstructive pulmonary diseases etc.

In order to stay healthy and disease free, people around the world practice meditation and other forms of relaxation techniques which prove to be effective for relaxation and for regulating body functions. Typically, meditation and exercises are taught by an experienced professional, as it requires proper guidance for achieving optimum results. However, a significant number of people who try to learn meditation and exercise techniques drop out or have difficulty in achieving desired results due to generic nature of the teaching. Meditation and other exercises cannot be quantified effectively except with the person's (also referred to as subject) feedback. Usually, after each session of meditation or exercise, a person's physiological parameters such as, heart rate, breathing rate, heart rate variability (HRV), blood pressure, stress levels, body movements etc. need to be accurately assessed and calculated for determining results of meditation or exercise on the person's body for achieving a desired body state. Conventionally, the techniques for calculating various physiological parameters requires one or more obtrusive techniques that are directly applied on a person. The obtrusive techniques applied may include, but are not limited to, wearable sensor device, electrodes, respiration sensing belts etc. The obtrusive techniques are bulky and a person may not be able to use them regularly and may require aid of another person, thereby making the process time consuming and exhaustive.

Further, it has been observed that existing unobtrusive techniques fail to effectively, efficiently and accurately provide desired physiological parameter measurements and are not able to operate and provide feedback to a subject in real-time when the subject is in a meditative state. Further, existing obtrusive and unobtrusive physiological parameters sensing techniques are not easily available, difficult to operate, not portable, not scalable and are expensive.

In light of the aforementioned drawbacks, there is a need for a system and a method which provides determining breathing rate as a biofeedback during a meditation or exercise session. There is a need for a system and a method which automatically and effectively quantifies the meditation and exercise session by optimizing physiological parameter measurements. Further, there is a need for a system and a method which aids in increasing the efficiency of the meditation and exercise session or process without disturbing the state of the meditating or exercising subject. Furthermore, there is a need for a system and a method for physiological parameters detection and regulation which is easily available, easily operable, portable, scalable and cost effective.

SUMMARY OF THE INVENTION

In various embodiments of the present invention, a system for determining breathing rate as a biofeedback during a meditation session or an exercise session is provided. The system comprises a computation engine executed by a processor and configured to extract a first biomarker, a second biomarker, a third biomarker and a fourth biomarker from physiological parameters associated with a subject by applying a pre-defined set of rules. The physiological parameters are received by the computation engine from a contactless sensor device. Further, the system comprises a feedback unit executed by the processor and configured to compute a first value in real-time as a function of the second biomarker, the third biomarker and the fourth biomarker. Further, the feedback unit is configured to determine a correlation between the first value and a time domain parameter of the fourth biomarker and a frequency domain parameter of the fourth biomarker. The first value is indicative of a stress level of the subject. Further, the feedback unit computes a second value by maximizing the time domain parameter of the fourth biomarker and minimizing the frequency domain parameter of the fourth biomarker based on the correlation. The second value is indicative of a reduced stress level of the subject. The feedback unit is further configured to transmit a biofeedback, in real-time, to a cue generation unit. The biofeedback is representative of a quantified data that is determined based on the second value. The quantified data is indicative of a modified second biomarker.

In various embodiments of the present invention, a method for determining breathing rate as a biofeedback during a meditation session or an exercise session is provided. The method comprises extracting a first biomarker, a second biomarker, a third biomarker and a fourth biomarker from physiological parameters associated with a subject by applying a pre-defined set of rules. The physiological parameters are received from a contactless sensor device. Further, the method comprises computing a first value in real-time as a function of the second biomarker, the third biomarker and the fourth biomarker. Further, the method comprises determining a correlation between the first value and a time domain parameter of the fourth biomarker and a frequency domain parameter of the fourth biomarker. The first value is indicative of a stress level of the subject. Further, the method comprises computing a second value by maximizing the time domain parameter of the fourth biomarker and minimizing the frequency domain parameter of the fourth biomarker based on the correlation. The second value is indicative of a reduced stress level of the subject. Further, the method comprises transmitting a biofeedback, in real-time to a cue generation unit. The biofeedback is representative of a quantified data that is determined based on the second value. The quantified data is indicative of a modified second biomarker.

BRIEF DESCRIPTION OF THE ACCOMPANYING DRAWINGS

The present invention is described by way of embodiments illustrated in the accompanying drawings wherein:

FIG. 13 and FIG. 13A is a flowchart illustrating a method for determining breathing rate as a biofeedback, in accordance with an embodiment of the present invention.

DETAILED DESCRIPTION OF THE INVENTION

The present invention discloses a system and a method for determining breathing rate as a biofeedback during a meditation or exercise session. The present invention provides for automatically and effectively quantifying effect of meditation or exercise on physiological parameters in an unobtrusive and contactless manner i.e. without disturbing state of the meditating or exercising person/subject. The present invention further provides for a system which has self-learning built-in-intelligent mechanism for adequately computing, regulating and optimizing the subject's physiological parameters. Further, the invention provides for a system and a method which efficiently provides a real-time feedback to guide the person or subject by enhancing the efficiency of the meditation or exercise session and achieve a relaxed state. The feedback provided comprises an adaptive feedback mechanism which is capable of adjusting itself based on detected physiological parameters of the subject. Further, the present invention provides for a system, which is portable, scalable and cost effective.

The disclosure is provided in order to enable a person having ordinary skill in the art to practice the invention. Exemplary embodiments herein are provided only for illustrative purposes and various modifications will be readily apparent to persons skilled in the art. The general principles defined herein may be applied to other embodiments and applications without departing from the spirit and scope of the invention. The terminology and phraseology used herein is for the purpose of describing exemplary embodiments and should not be considered limiting. Thus, the present invention is to be accorded the widest scope encompassing numerous alternatives, modifications and equivalents consistent with the principles and features disclosed herein. For purposes of clarity, details relating to technical material that is known in the technical fields related to the invention have been briefly described or omitted so as not to unnecessarily obscure the present invention.

The present invention would now be discussed in context of embodiments as illustrated in the accompanying drawings.

Figure 1:
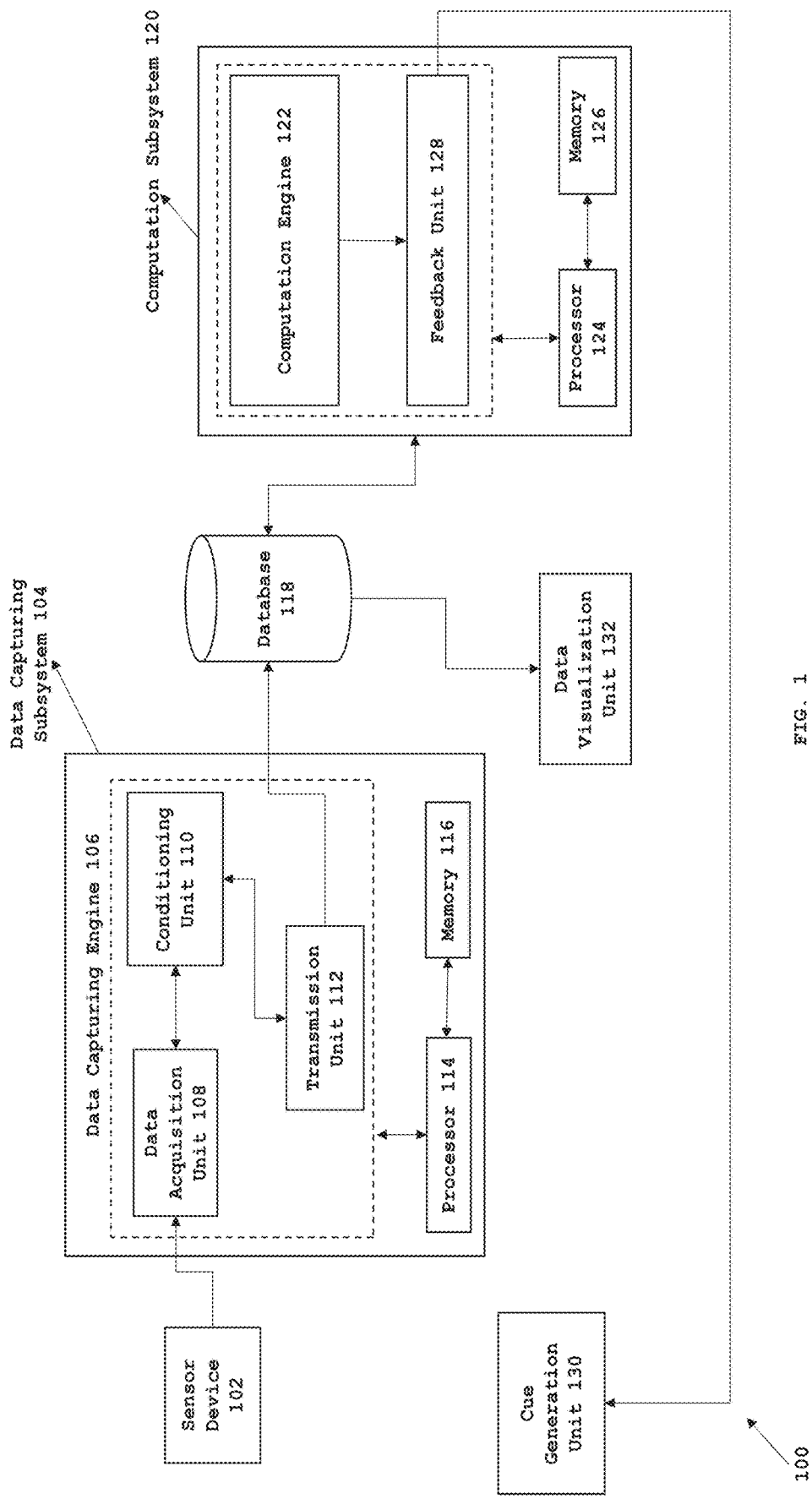
FIG. 1 is a block diagram of a system for determining breathing rate as a biofeedback, in accordance with an embodiment of the present invention.

FIG. 1 is a block diagram of a system for determining breathing rate as a biofeedback, in accordance with various embodiments of the present invention.

In an embodiment of the present invention, the system 100 comprises a sensor device 102, a data capturing subsystem 104, a database 118, a computation subsystem 120, a cue generation unit 130 and a data visualization unit 132.

In an embodiment of the present invention, the sensor device 102 comprises an array of sensors which are placed in a housing at the subject's end. The sensor device 102 is specifically designed for carrying out various embodiments of the present invention. In an exemplary embodiment of the present invention, the sensor device 102 is of a very low thickness, preferably of around 3 mm and has an outer casing for protecting and covering the housing. The outer casing may be a robust and rugged thin cover made of a material, but is not limited to, a mesh, latex, cloth, polymer etc. which firmly holds the array of sensors in a fixed position. In an exemplary embodiment of the present invention, the sensor device 102 comprises, vibroacoustic sensors, piezoelectric sensors etc. The sensor device 102 may be of a particular shape which may include, but is not limited to, rectangular, square, circular, oval etc. The sensor device 102 is capable of being folded and is a light weight device. In various embodiments of the present invention, the sensor device 102 is used in a non-invasive and contactless manner with respect to the subject. The sensor device 102 may be placed under a medium such as a yoga mat, mattress, cushion etc. on which a subject may sit, stand or lie for performing the meditation or exercise techniques. The sensor device 102 may be aligned in any resting position such as, but is not limited to, sitting position, lying down position etc. with respect to the subject.

In an embodiment of the present invention, in operation, the sensor device 102, positioned in a contactless manner, with respect to the subject, at the subject's end, is configured to capture micro-vibrations corresponding to physiological parameters of the subject, who is in a state of meditation or exercise, as analog data signals. The sensor device 102 is capable of capturing micro-vibrations received through a medium placed between the subject and sensor device 102. For example, the micro-vibrations may be captured through a medium ranging from a thin surface such as a yoga mat to a thick surface such as a 20-inch mattress. The micro-vibrations captured by the sensor device 102 may include, but are not limited to, ballistocardiographic (BCG) signals associated with physiological parameters of the subject such as, breathing rates, heart rates, heart movements, chest movements, cardiac frequency etc. which may represent state of the subject at the time of meditation or exercise. Further, the sensor device 102 is configured to convert the captured micro-vibrations, which are analog signals, into micro-voltage digital signals. The micro-voltage digital signals may be in the range of between 0-3.3 V.

In an embodiment of the present invention, the data capturing subsystem 104 is configured to receive the micro-voltage digital signals from the sensor device 102 corresponding to the physiological parameters of the subject. The sensor device 102 may be connected to the data capturing subsystem 104 via a wired or wireless connection. The data capturing subsystem 104 may be positioned at the subject's location. In various embodiments of the present invention, the data capturing subsystem 104 comprises a data capturing engine 106, a processor 114 and a memory 116. The data capturing engine 106 comprises multiple units that operate in conjunction with each other for capturing and transmitting the data received from the sensor device 102 to the database 118. The various units of the data capturing engine 106 are operated via the processor 114 specifically programmed to execute instructions stored in the memory 116 for executing respective functionalities of the units of the engine 106 in accordance with various embodiments of the present invention.

In an embodiment of the present invention, the data capturing engine 106 comprises a data acquisition unit 108, a conditioning unit 110 and a transmission unit 112. The data acquisition unit 108 of the data capturing engine 106 is configured to receive the micro-voltage digital signals from the sensor device 102 and record the received micro-voltage digital signal in a pre-defined data recording format. The pre-defined data recording format may include, but is not limited to, a chronological order.

In an embodiment of the present invention, the data acquisition unit 108 transmits the recorded micro-voltage digital signal to the conditioning unit 110. The conditioning unit 110 is configured to amplify the micro-voltage digital signal for maximizing the resolution of the micro-voltage digital signal, as desired, to accurately process the micro-voltage digital signal for efficient detection of subject's physiological parameters. The maximization of resolution of micro-voltages digital signal is carried out without data loss or information loss that may occur due to clipping. Further, amplification and resolution maximization of the micro-voltage digital signal aids the sensor device 102 to operate with any thickness and construction of medium between the sensor device 102 and the subject. The conditioning unit 110 is configured with multiple amplification capabilities for amplifying the micro-voltage digital signal depending upon the strength of the received micro-voltage signal from the data acquisition unit 108. In an exemplary embodiment of the present invention, the multiple amplification capabilities embedded in the conditioning unit 110 provides, but are not limited to, eight different amplification options that amplify the micro-voltages between the range of 15× to 2500×. The conditioning unit 110 is configured to automatically calibrate and select the amplification option. The conditioning unit 110 is based on a sensitivity shifting mechanism for automatically calibrating and selecting the amplification option. The sensitivity shifting mechanism depends upon the level of strength of the micro-voltage digital signal received from the sensor device 102 when the subject is in a meditation or exercise state.

In an embodiment of the present invention, the transmission unit 112 of the data capturing engine 106 is configured to transmit the amplified micro-voltage digital signal to the database 118. The amplified micro-voltage digital signal is transmitted to the database 118 via a communication channel (not shown). The communication channel (not shown) may include, but is not limited to, a wire or a logical connection over a multiplexed medium, such as, a radio channel in telecommunications and computer networking. Examples of telecommunications and computer networking may include a local area network (LAN), a metropolitan area network (MAN), a wide area network (WAN) or any wired or wireless network, such as, but not limited to, Wi-Fi, Bluetooth® Classic, Bluetooth® Low Energy etc. In an exemplary embodiment of the present invention, the database 118 may be positioned at the location of the sensor device 102 and the data capturing subsystem 104. For example, the database 118 may be installed on a smartphone, tablet, laptop, computer system etc. of the subject. In another exemplary embodiment of the present invention, the database 118 may be positioned at a location remote to the sensor device 102 and the data capturing subsystem 104, such as, in a cloud based server. In an embodiment of the present invention, the database 118 is configured to store the micro-voltage digital signal in a pre-defined data storage format which may include, but is not limited to, one or more datasets in a chronological order.

In an embodiment of the present invention, the database 118 is configured to transmit the stored micro-voltage datasets corresponding to physiological parameters of the subject, to the computation subsystem 120. The computation subsystem 120 is an intelligent and self-learning subsystem configured to automatically analyze complex data, extract patterns of events associated with physiological parameters, calculate the physiological parameter, compute the desirable physiological parameters information related to the subject by utilizing one or more of the cognitive computing techniques. The cognitive computing techniques may include, but is not limited to, artificial intelligence, machine learning, deep learning, and pattern recognition technique. In an exemplary embodiment of the present invention, the computation subsystem 120 may be positioned at a location of the sensor device 102 and the data capturing subsystem 104, for example, the computation subsystem 120 may be installed in a smartphone, tablet, laptop, computer system etc. of the subject. In another exemplary embodiment of the present invention, the computation subsystem 120 may be positioned at a location remote to the sensor device 102 and the data capturing subsystem 104, such as, in a cloud based server.

In an embodiment of the present invention, the computation subsystem 120 comprises a computation engine 122, a feedback unit 128, a processor 124 and a memory 126. The computation engine 122 comprises various units which work in conjunction with each other for efficiently analyzing, processing and identifying various physiological parameters from the micro-voltage datasets. The various units of the engine 122 are operated via the processor 124 specifically programmed to execute instructions stored in the memory 126 for executing respective functionalities of the computation engine 122 in accordance with various embodiments of the present invention. Further, the feedback unit 128 is operated via the processor 124 specifically programmed to execute instructions stored in the memory 126 for executing respective functionalities in accordance with various embodiments of the present invention.

Figure 2:
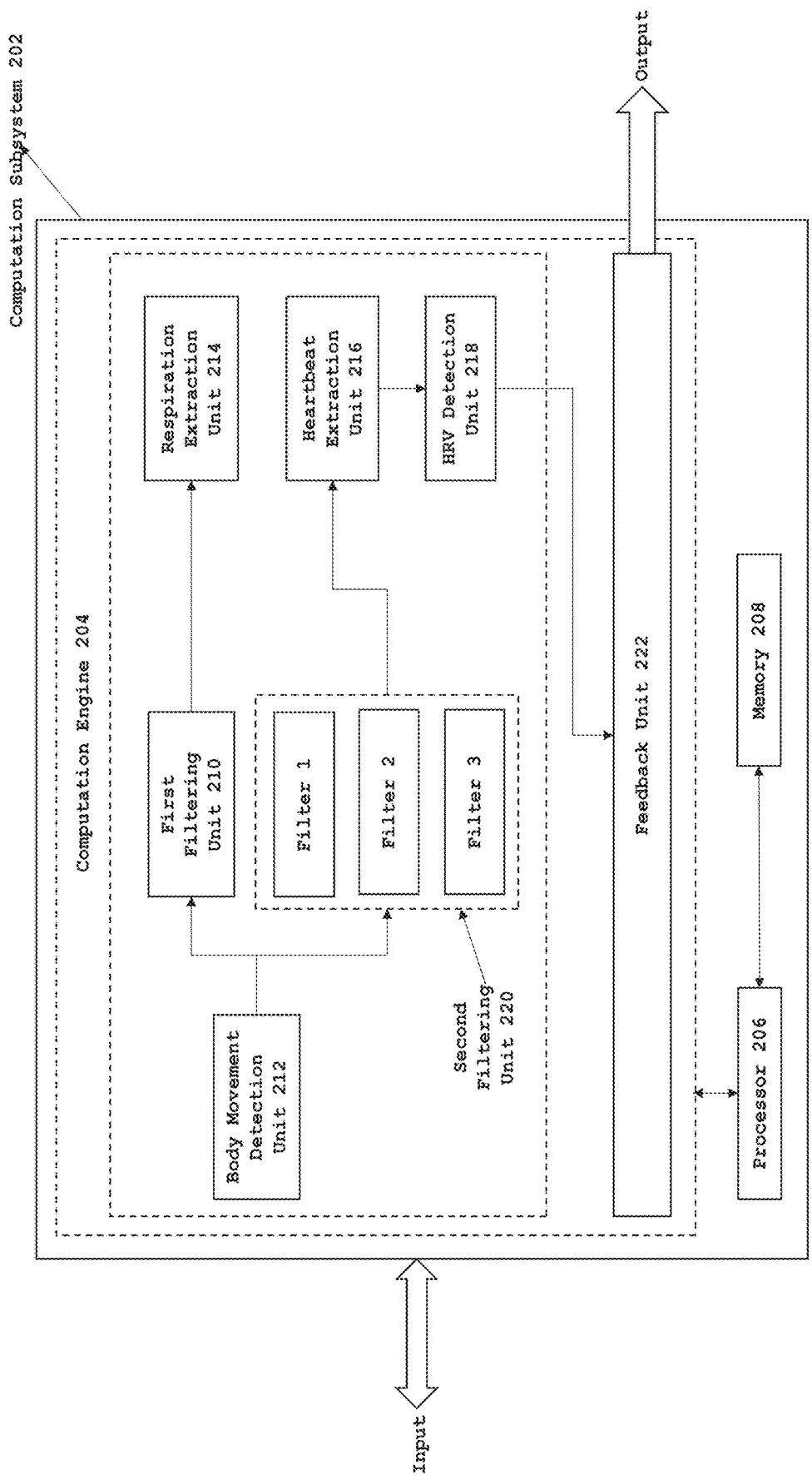
FIG. 2 is a detailed block diagram of a computation subsystem, in accordance with an embodiment of the present invention.

FIG. 2 is a detailed block diagram of a computation subsystem 202, in accordance with various embodiments of the present invention. The computation subsystem 202 interfaces with database 118 (FIG. 1). The computation subsystem 202 is configured to invoke the database 118 (FIG. 1) for retrieving the stored micro-voltage datasets corresponding to physiological parameters of the subject.

In an embodiment of the present invention, the computation subsystem 202 comprises a computation engine 204, a processor 206 and a memory 208. The computation engine 204 comprises various units which work in conjunction with each other for efficiently analyzing, processing and identifying various physiological parameters. The various units of the engine 204 are operated via the processor 206 specifically programmed to execute instructions stored in the memory 208 for executing respective functionalities of the computation engine 204 in accordance with various embodiments of the present invention.

The computation engine 204 comprises a body movement detection unit 212, a first filtering unit 210, a second filtering unit 220, a respiration extraction unit 214, heartbeat extraction unit 216 and a heart rate variability (HRV) parameters detection unit 218.

In an embodiment of the present invention, the computation subsystem 202 is configured to apply a set of pre-defined rules for processing micro-voltage datasets corresponding to the physiological parameters related to one or more subjects. The set of pre-defined rules are based on various empirical studies of physiological parameter data collected from prior experimentation, physiological parameter data collected from various subjects and data collected based on learning pattern developed over a period of time. In various embodiments of the present invention, the set of pre-defined rules may be updated from time to time by the subsystem 202. The computation engine 204 of the computation subsystem 202 is configured to apply the set of rules for effective analysis, processing and identification of physiological parameters.

Figure 3:
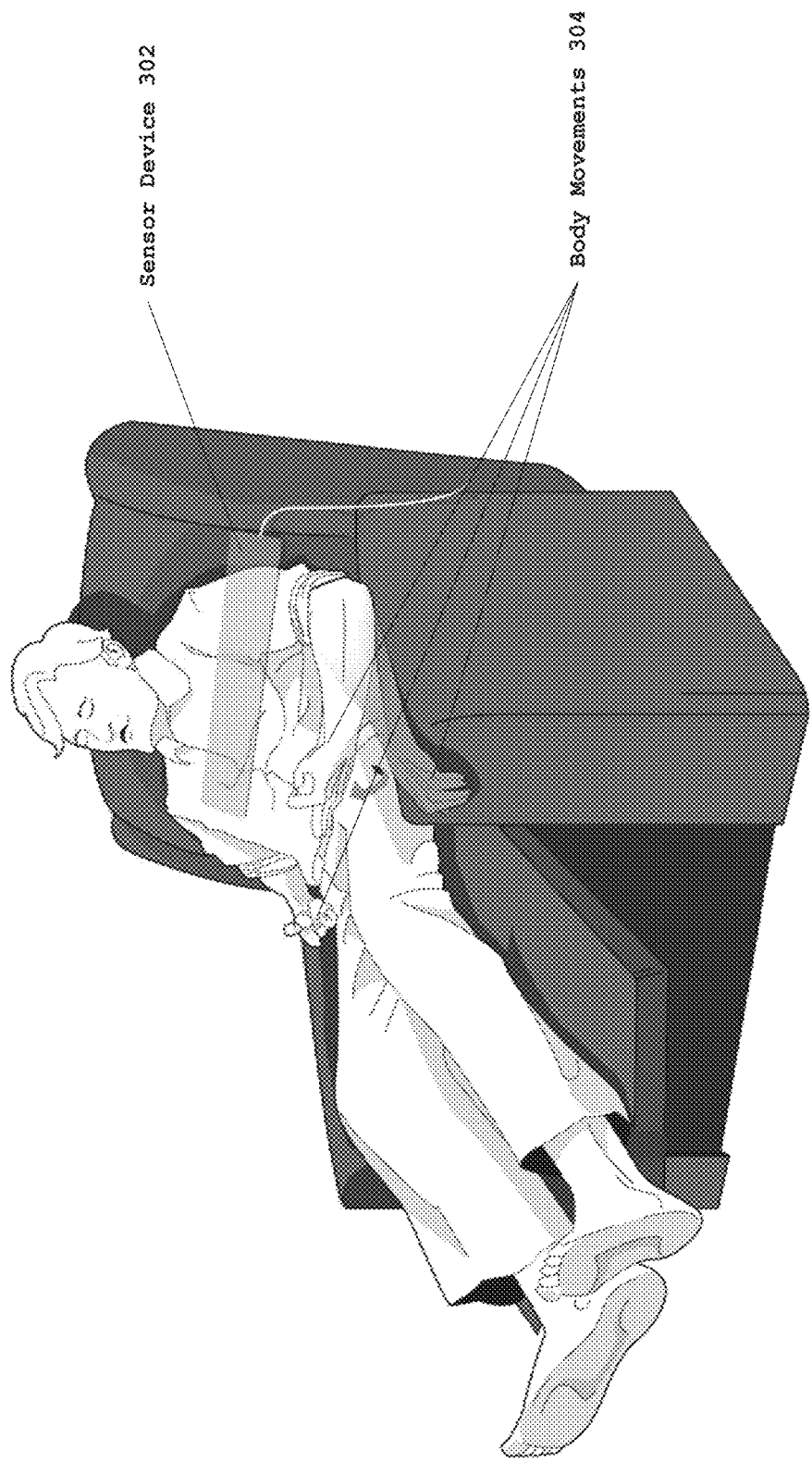
FIG. 3 is an exemplary diagram illustrating a subject in a meditation state performing various body movements, in accordance with an embodiment of the present invention.
Figure 4:
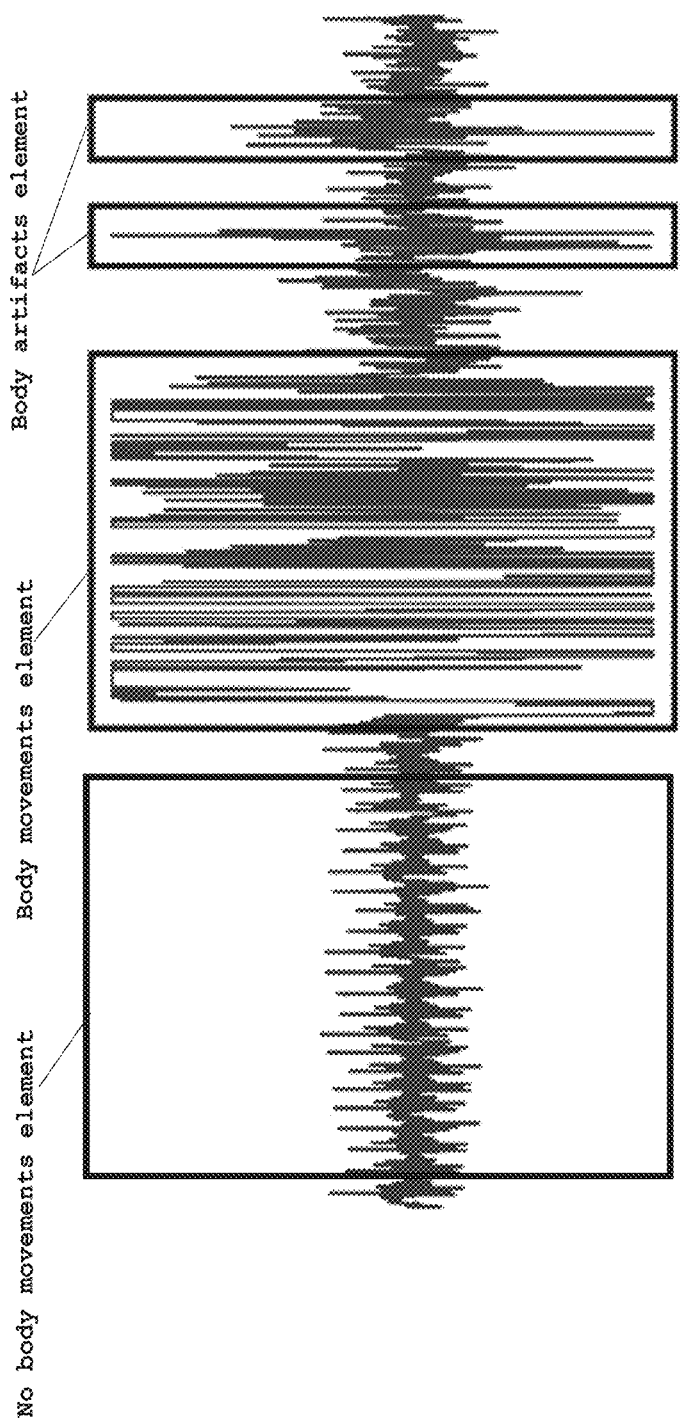
FIG. 4 illustrates a graphical representation of subject's no body movements element, body movements element and body artifacts element, in accordance with an embodiment of the present invention.

In operation, in an embodiment of the present invention, the body movement detection unit 212 of the computation engine 204 is configured to receive the stored micro-voltage dataset from the database 118 (FIG. 1). The body movement detection unit 212 subsequently applies a first set of rules on the micro-voltage datasets to extract a first biomarker and select an element from the first biomarker. The first biomarker represents a 'body movements' element, a 'no body movements' element and a 'body artifacts' element corresponding to the subjects. For instance, as illustrated in FIG. 3 when the subject is in a meditation state, while sitting on a chair, he/she may make certain hand or body movements 304 which are detected by the sensor device 302 and extracted at the body movement detection unit 212 as the first biomarker. In an exemplary embodiment of the present invention, the body movement detection unit 212 is configured to extract the first biomarker by processing the micro-voltage dataset to obtain multiple dataset points which are individual points in an n-dimensional space. The body movement detection unit 212 is configured to further apply unsupervised cognitive techniques such as, but not limited to, density based spatial clustering of applications with noise (DBSCAN) technique etc. for clustering similar dataset points in the n-dimensional space to identify the first biomarker and selecting the 'no body movements' element. In an exemplary embodiment of the present invention, the similar dataset points are clustered by the body movement detection unit 212 by calculating a Euclidean distance and further calculating a standard deviation between each point in the search space. In an exemplary embodiment of the present invention, the dataset points clustered may be classified as 'body movements' element, 'no body movements' element and 'body artifacts' element, as shown in graphical representation illustrated in FIG. 4. Example of the 'body movements' element and 'body artifacts' element may include, but are not limited to, unwanted body movements, twitches, external mechanical or electrical noises etc. The body movement detection unit 212 is configured to remove and isolate the clusters relating to 'body movements' element and 'body artifacts' element from the physiological parameter datasets after clustering, thereby selecting the 'no body movement' element. The 'no body movements' element is selected for determining physiological parameters, which otherwise would not have been distinguishable due to 'body movements' element and 'body artifacts' element.

Figure 5:
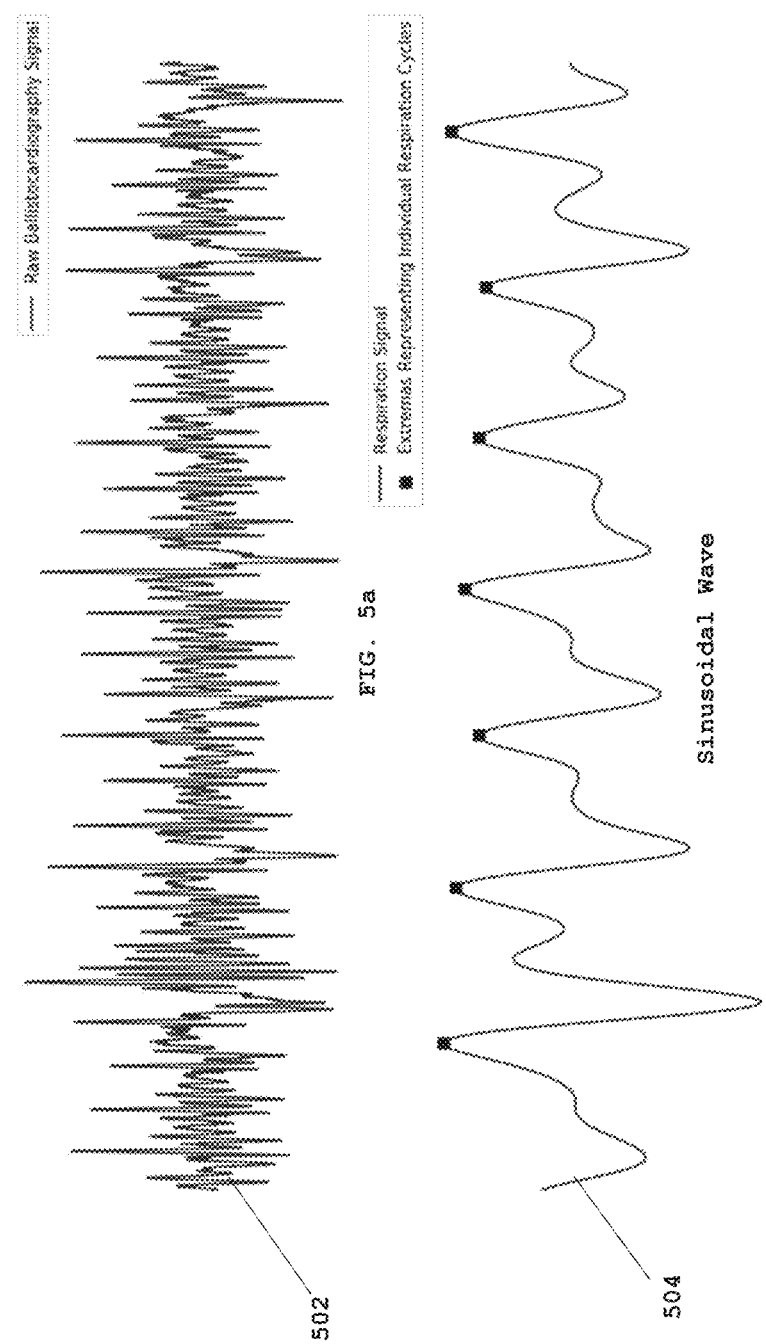
FIG. 5a illustrates a ballistocardiographic (BCG) signal corresponding to physiological parameters of a subject and FIG. 5b illustrates a sinusoidal waveform respiratory signal extracted from the BCG signal, in accordance with an embodiment of the present invention.
Figure 6:
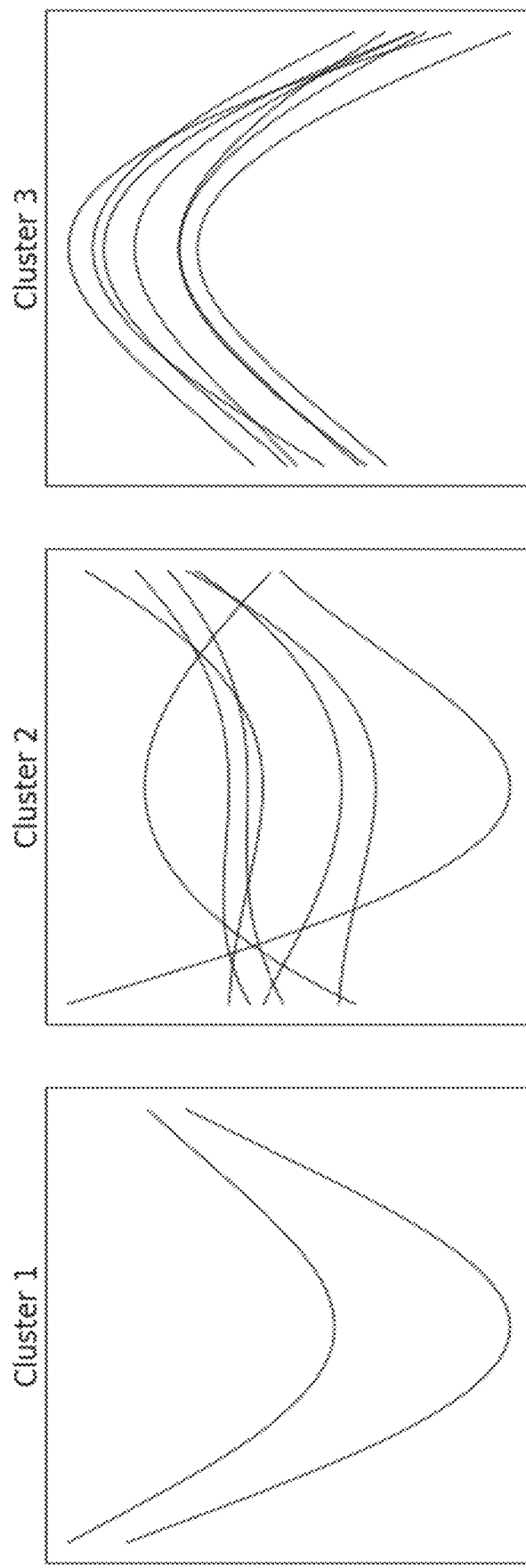
FIG. 6 illustrates respiration signal template clusters, in accordance with an embodiment of the present invention.

In an embodiment of the present invention, the first filtering unit 210 of the computation engine 122 is configured to receive the 'no body movements' element from body movement detection unit 212. The first filtering unit 210 may include a digital signal processing filter, such as, but is not limited to, a Butterworth filter. The first filtering unit 210 may be tuned at a frequency range of between 0.1 Hz to 1 Hz. The first filtering unit 210 applies a second set of rules from the pre-defined set of rules to process the 'no body movements' element to extract a second biomarker. FIG. 5a illustrates a raw ballistocardiographic (BCG) signal 502 corresponding to physiological parameters and FIG. 5b illustrates the second biomarker which represents the respiratory signal extracted from the selected 'no body movement' element. The terms respiration signal and breathing rate relates to breathing of the subject and has been used interchangeably throughout the specification. Therefore, second biomarker may also relate to breathing rate of the subject. The respiration signal may be extracted in the form of a sinusoidal wave 504 which may also include some noise elements as illustrated in FIG. 5. Further, the first filtering unit 210 is configured to remove the noise element present in the sinusoidal wave and subsequently provide an output comprising a uniform sinusoidal wave representing the breathing cycles as a respiratory signal. The computation engine 204 further applies the second set of rules for appropriately transmitting the respiratory signal in the form of uniform sinusoidal wave to the respiration extraction unit 214. The respiration extraction unit 214 is configured to process the sinusoidal wave representing the respiratory signal for extracting and computing each breathing cycle associated with the subject. The breathing cycles are extracted and computed based on total number of maximas and minimas present in the sinusoidal wave. The respiration extraction unit 214 is further configured to extract maximas and minimas of the sinusoidal wave separately into multiple template forms. In an exemplary embodiment of the present invention, all the extremas of the sinusoidal signal are computed and some points before and after the extrema points are taken to form the template. The extracted templates may comprise either maxima or minima of the sinusoidal wave representing breathing cycles. In an exemplary embodiment of the present invention, the respiration extraction unit 214 is configured to apply unsupervised machine learning based techniques such as, but not limited to, data clustering techniques on the extracted and formed templates. The templates comprising similar patterns i.e. either maxima or minima are clustered together by the respiration extraction unit 214 in one cluster. Similar template clusters are therefore formed comprising either maxima or minima associated with the breathing cycles. In an exemplary embodiment of the present invention, the respiration extraction unit 214 is configured to segregate the formed templates, preferably, into three clusters, i.e. cluster 1, cluster 2 and cluster 3 as illustrated in FIG. 6, for adequately determining the breathing cycles based on clustering techniques such as, but is not limited to, K-means++ clustering. In an exemplary embodiment of the present invention, the templates are segregated into three clusters by computing Euclidean distances between the templates. Further, out of the three template clusters, a first principal template is selected by the respiration extraction unit 214 from the formed clusters. For instance, cluster 3 is selected as the first principal template in this embodiment of the present invention. The first principal template is representative of maximum number of breathing instances or respiration cycles. The first principal template is selected based on the Euclidean distance of cluster centers with respect to each other. In particular, the template cluster farthest from the other two template clusters is selected as the first principal template. Advantageously, respiration extraction unit 214 is capable of providing 95% accuracy for identification of each respiratory or breathing cycle, in accordance with various embodiments of the present invention.

Figure 7:
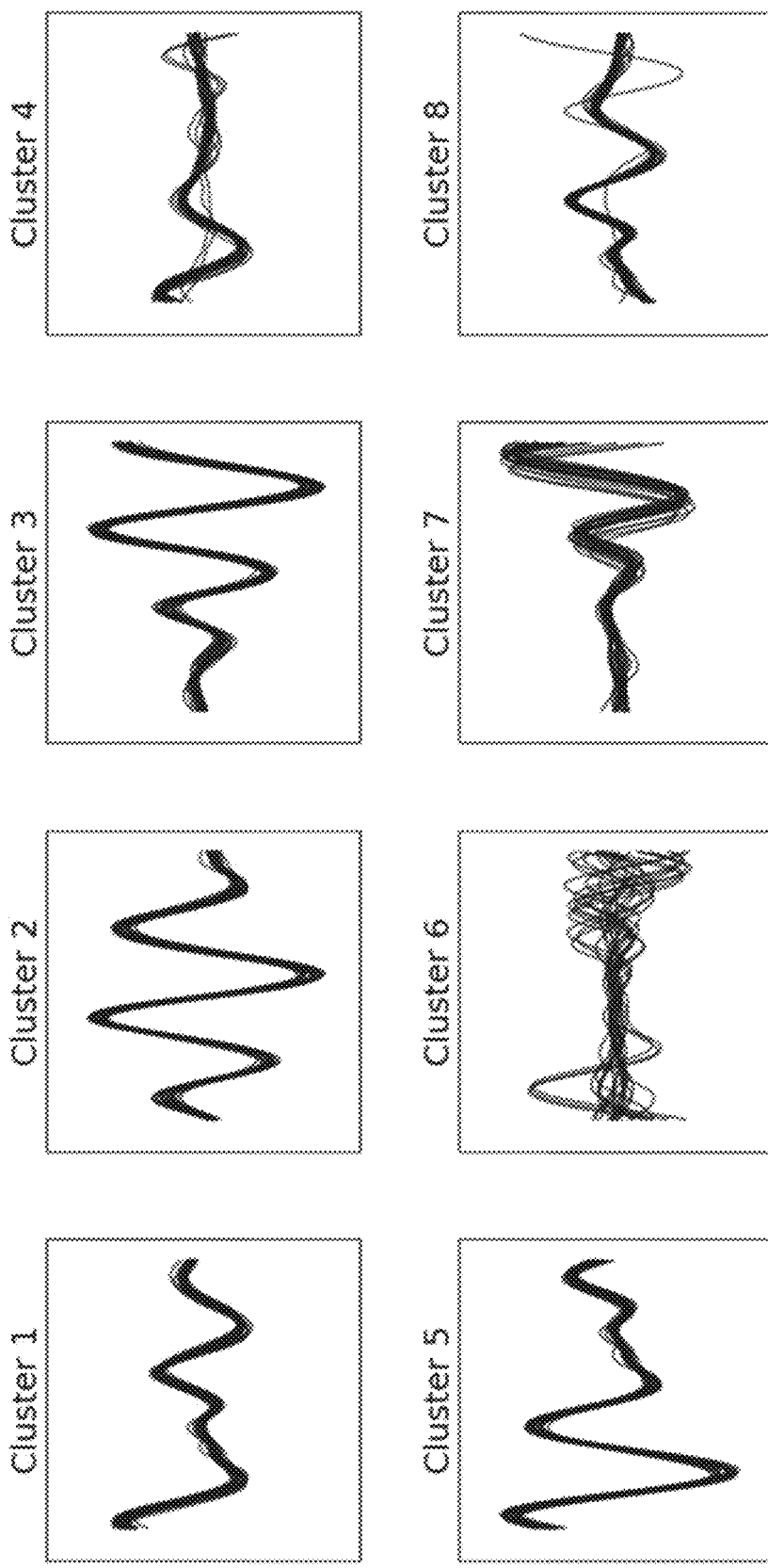
FIG. 7 illustrates eight clusters of clustered heartbeat signal templates, in accordance with an embodiment of the present invention.

In an embodiment of the present invention, the second filtering unit 220 of the computation engine 204 is configured to receive the selected 'no body movements' element from the body movement detection unit 212. The second filtering unit 220 then applies a third set of rules, from the pre-defined set of rules, to filter and extract a third biomarker. The third biomarker is representative of a heartbeat or cardiac signal datasets in the form of a waveform. The heartbeat or cardiac signal dataset waveforms are representative of heartbeats that may occur when the subject is in a meditation or exercise state. The second filtering unit 220 may include, but is not limited to, digital signal processing filters. The second filtering unit 220 further comprises three separate filters i.e. filter 1, filter 2 and filter 3 working in conjunction with each other. The second filtering unit 220 comprising the three filters is specifically designed and configured to extract each heartbeat from the cardiac signals in the form of multiple heartbeat signal waveforms. The computation engine 204 further applies the third set of rules for appropriately transmitting the multiple heartbeat signal waveforms to the heartbeat extraction unit 216. The heartbeat extraction unit 216 is configured to process and analyze the received multiple heartbeat signal waveforms for forming multiple templates corresponding to multiple heartbeat signal waveforms. In an exemplary embodiment of the present invention, the signal between three continuous maximas and two continuous minimas are processed to form the heartbeat waveform signal template. The heartbeat extraction unit 216 subsequently assesses similarity between the heartbeat signal templates by applying unsupervised machine learning techniques such as, but is not limited to, clustering techniques for clustering the similar templates. In an exemplary embodiment of the present invention, the heartbeat extraction unit 216 is configured to cluster the formed templates, preferably, into eight clusters based on the Euclidean distance technique as illustrated in FIG. 7. Further, a second principal template is selected by the heartbeat extraction unit 216 from the formed eight template clusters based on the frequency composition of the centroid template. The second principal template is representative of a template cluster having a maximum number of heartbeats. For instance, as illustrated in FIG. 7, cluster 2 has a maximum number of heartbeats, and is therefore selected as the second principal template. In an exemplary embodiment of the present invention, the second principal template may further be selected based on a frequency analysis technique, a fast Fourier transform technique etc. The second principal template may comprise highest power in a desired frequency range.

Figure 8:
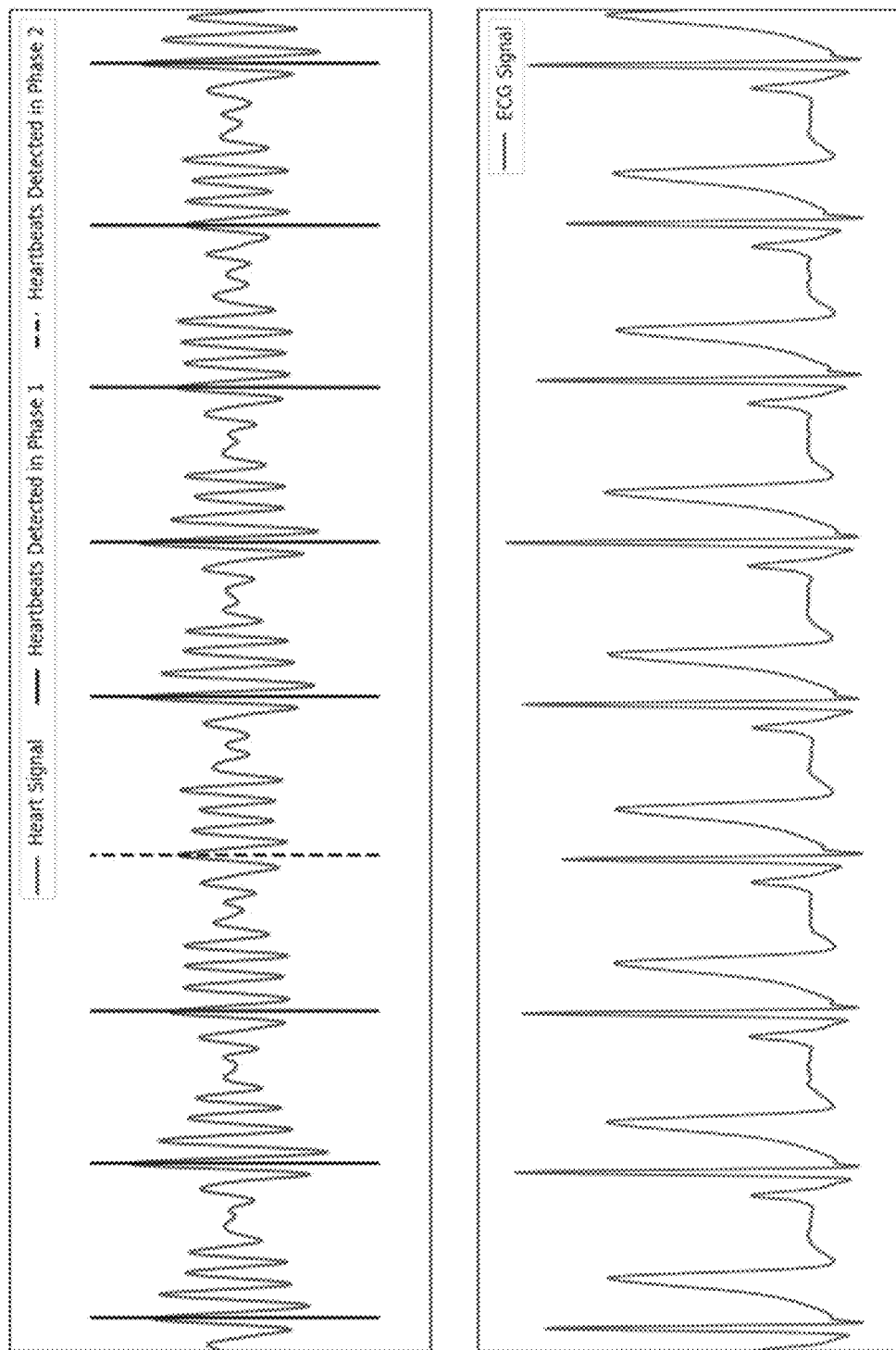
FIG. 8 illustrates a heartbeat signal detected, in accordance with an embodiment of the present invention, as compared to a conventional electrocardiogram (ECG)

In an embodiment of the present invention, one or more extracted heartbeats in the template form may be clustered by the heartbeat extraction unit 216 in a different cluster other than the clusters utilized for selecting the second principal template. The heartbeat extraction unit 216 is configured to analyze the clustered heartbeat waveform signal templates to identify potential instances of missing heartbeats by analyzing abnormal intervals between neighboring heartbeats determined based on the second principal template. In an exemplary embodiment of the present invention, the identification of missing heartbeats is carried out based on correlation assessment techniques such as, but is not limited to, a Pearson correlation technique. Consequently, the missing heartbeats from the second principal template are also detected and clustered appropriately. In an exemplary embodiment of the present invention, an abnormal interval in the clustering of the heartbeat templates is detected if the time interval between two successive heartbeats is found to be considerably more than the average time interval between the successive heartbeats for a pre-determined period. The templates in that interval are then compared to the centroid of the selected cluster and the Pearson correlation coefficient is computed. Thereafter, if any template has significant Pearson correlation coefficient, it is selected as a heartbeat. FIG. 8 illustrates a heartbeat signal which is detected based on the second principal template detected in the phase 1 and the missing heartbeat detected in the phase 2. Advantageously, the heartbeat extraction unit 216, in accordance with various embodiments of the present invention, is capable of providing 96% accuracy in identification of each heartbeat in comparison to conventional electrocardiogram (ECG) technique as illustrated in FIG. 8.

In an embodiment of the present invention, the heartbeat extraction unit 216 after detecting each individual heartbeat based on the second principal template is configured to communicate with the heart rate variability (HRV) detection unit 218 for computing and determining the fourth biomarker. The fourth biomarker is representative of heart rate variability (HRV) parameters associated with the heartbeats. The HRV parameters are representative of variation in the time interval between each heartbeat. The detection of HRV parameters aids in determining the state of autonomic nervous system (ANS) of the subject for effectively determining and evaluating stress levels of the subject at the beginning of meditation or exercise session until the end of the session. Therefore, in order to measure HRV parameters (fourth biomarker), the HRV detection unit 218 is configured to compute variation in the beat-to-beat time intervals. In particular, the HRV detection unit 218 is configured to compute HRV parameters by computing time and frequency domain parameters related to each heartbeat interval. The time domain parameters computed may include, but are not limited to, standard deviation of normal-to-normal intervals (SDNN), standard deviation of the average normal-to-normal intervals (SDANN), root mean square of successive differences (RMSSD) and proportion of NN50 (pNN50). Further, the frequency domain parameters computed may include, but is not limited to, very low frequency (VLF), low frequency (LF), high frequency (HF) and ratio of LF to HF (LF/HF). The HRV detection unit 218 upon receiving the detected heartbeats from the heartbeat detection unit 216 is configured to firstly determine time domain parameters by providing a timestamp for each heartbeat interval and subsequently determine the frequency domain parameters. In an exemplary embodiment of the present invention, the HRV detection unit 218 is configured to firstly compute the time domain parameters associated with heartbeats. The HRV detection unit 218 then determines SDNN and SDANN parameters associated with a heartbeat. SDNN is computed by determining standard deviation of NN intervals for every 30 seconds. Further, SDANN is computed as standard deviation of the average NN intervals calculated for over short intervals of time period, preferably, for 5 minutes. SDNN further provides all the cyclic components responsible for variability in the period of recording, and therefore it represents the total variability. Further, RMSSD is computed by calculating the square root of the mean of the squares of the successive differences between adjacent NNs. Subsequently, pNN50 is computed by calculating the proportion of NN50 divided by total numbers of NNs. NN50 count, therefore, is the mean number of times per hour in which the change in consecutive normal (NN) intervals exceeds 50 milliseconds. Further, after computing time domain parameters, the HRV detection unit 218 is configured to compute frequency domain parameters. The HRV detection unit 218 assigns bands of frequency and subsequently determines the number of NN intervals that match each band. The frequency bands may comprise high frequency (HF) in the range of 0.15 to 0.4 Hz, low frequency (LF) in the range of 0.04 to 0.15 Hz and very low frequency (VLF) in the range of 0.0033 to 0.04 Hz. Further, after assigning the frequency bands, the HRV detection unit 218 analyzes the frequency bands for determining the frequency domain parameters. In an exemplary embodiment of the present invention, the HRV detection unit 218 analyzes the frequency bands based on a parametric power spectral density (PSD) and non-parametric PSD for determining power distribution across frequencies. In another exemplary embodiment of the present invention, the HRV detection unit 218 computes frequency parameters based on techniques such as, but are not limited to, Fast Fourier Transform (FFT) and Lomb-Scargle (LS) periodogram.

In an embodiment of the present invention, the computation subsystem 202 is further configured to transmit the extracted first, second, third and fourth biomarker to the database 118 (FIG. 1) for storage. The stored data is capable of being retrieved for viewing by the subject via the data visualization unit 132 (FIG. 1).

In an embodiment of the present invention, the feedback unit 222 is configured to receive the second, third and fourth biomarker from the computation engine 204. The second, third and fourth biomarker received by the feedback unit 222 are representative of breathing rates of the subject, heart rate of the subject and HRV parameters associated with the heartbeat. The feedback unit 222 is further configured to provide a feedback in the form of a biofeedback in real-time to the subject via the cue generation unit 130 for guiding and aiding the subject to achieve a relaxation state during the meditation or exercise session. In various embodiments of the present invention, the feedback unit 222 provides capability for regulating breathing rate which is in control of the subject by computing a second value from a first value that are computed as a function of second, third and fourth biomarker. The first value is indicative of stress levels of the subject. The second value is indicative of a reduced stress level of the subject. The feedback unit 222 therefore optimizes the meditation or exercise session based on guidance provided in the form of regulated breathing rate, to which the subject may adapt for achieving the most relaxed and stress free state.

In particular, the feedback unit 222, in order to optimize the meditation or exercise session, computes the first value associated with each of the biomarkers. In an exemplary embodiment of the present invention, the first value is computed as a function of second, third and fourth biomarker that represents breathing rate, heart rate and HRV parameters. In one example, the feedback unit 222 computes the first value as a non-linear function of breathing rate, heart rate and time domain HRV parameters and frequency domain HRV parameters.

In an embodiment of the present invention, the feedback unit 222 computes the second value by regulating the computed first value. In an exemplary embodiment of the present invention, the feedback unit 222 is configured to determine a correlation between the first value and a time domain parameter of the fourth biomarker and a frequency domain parameter of the fourth biomarker for computing a second value. In an exemplary embodiment of the present invention, the correlation is representative of an inverse relationship between the first value and the time domain parameter of the fourth biomarker and a direct relationship between the first value and the frequency domain parameter of the fourth biomarker. In particular, the first value is inversely proportional to SDNN, RMSSD, pNN50 and HF parameters associated with the HRV parameters and directly proportional to the LF and LF/HF parameters associated with the HRV parameters. The second value is computed by maximizing SDNN parameter associated with the time domain HRV parameter (fourth biomarker) and minimizing LF/HF parameter associated with the frequency domain HRV parameter (fourth biomarker). Therefore, by maximizing SDNN parameter and minimizing LF/HF parameter, the first value associated with the subject reduces and the reduced value is the second value. In exemplary embodiment of the present invention, the feedback unit 222 utilizes a regression model based technique with back propagation for optimizing the meditation or exercise session by adequately computing the second value.

In yet another embodiment of the present invention, the feedback unit 222 is subsequently configured to transmit a biofeedback, in real-time, to the cue generation unit 130. The biofeedback is representative of a quantified data that is determined based on the second value. The quantified data is indicative of a modified second biomarker i.e. breathing rate which is obtained based on the computed second value. In an exemplary embodiment of the present invention, the breathing rate is modified in every 5-10 seconds. The modified breathing rate aids the subject in achieving a relaxed state.

Figure 9:
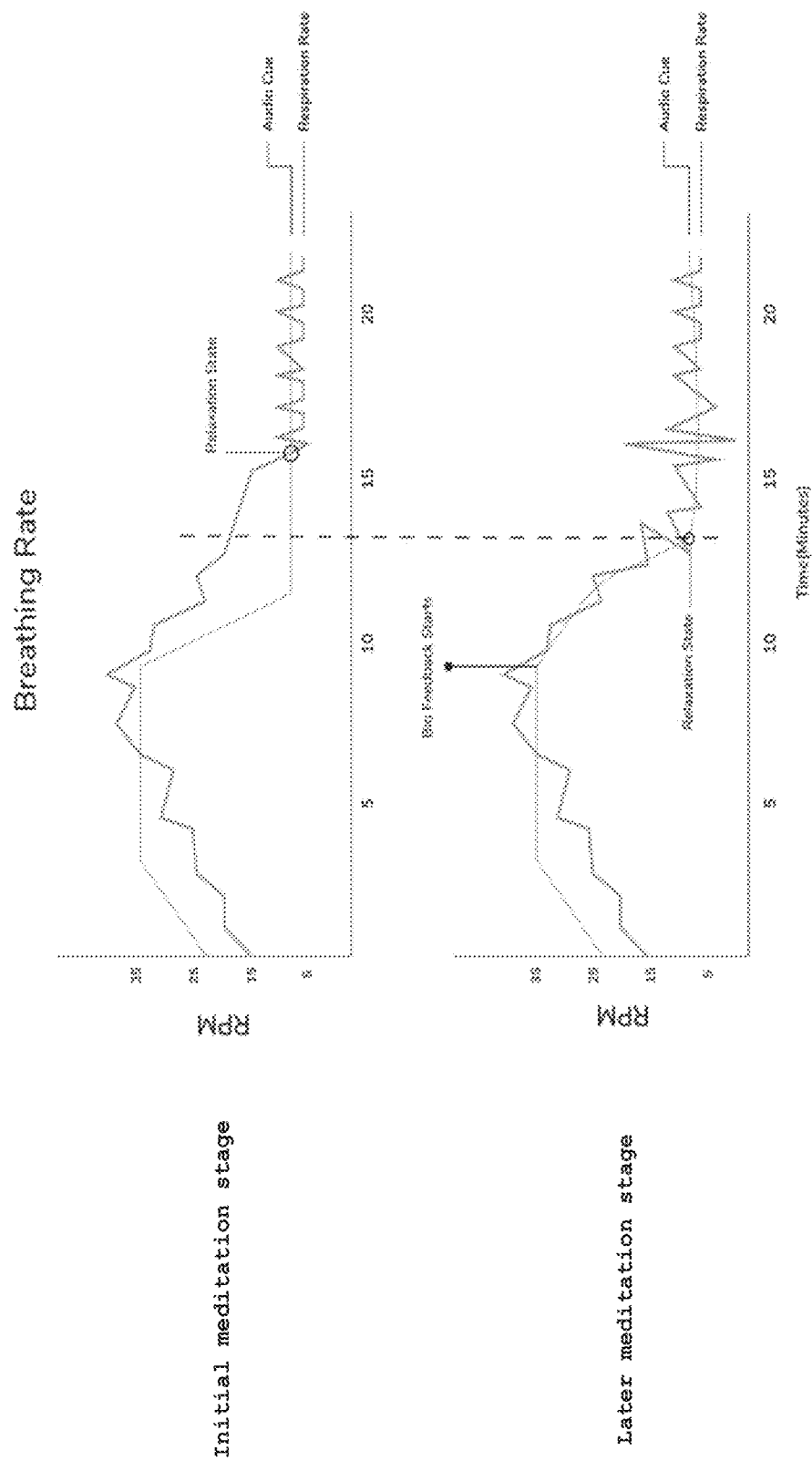
FIG. 9 illustrates a graphical representation depicting an improved breathing rate at a later stage of meditation with breathing rate cue, in accordance with an embodiment of the present invention as compared to the breathing rate at the initial meditation stage without breathing rate cue.

In another embodiment of the present invention, the feedback unit 222 communicates with the cue generation unit 130 for communicating the modified breathing rate to the subject in real-time during the meditation or exercise session. The cue generation unit 130 is positioned at the location of the subject. By providing a modified breathing rate to the subject as biofeedback, the dependent physiological levels such as heart rate and heart rate variability (HRV) parameters are also controlled. The cue generation unit 130 is configured to provide the modified breathing rate as a cue to the subject in the form of, but is not limited to, an audio, a video and haptic feedback. FIG. 9 illustrates a graphical representation depicting an improved breathing rate at a later stage of meditation with a breathing rate cue in accordance with an embodiment of the present invention, as compared to the breathing rate at the initial meditation stage without breathing rate cue.

In an embodiment of the present invention, the subject performing meditation or exercise may be able to view, listen, sense or feel the generated cue. Further, the subject performing the meditation or exercise may be able to get a personalized cue from the cue generation unit 130. The cue may be viewed, listened, sensed or felt by that subject. The personalized cue is provided to the subject, if subject is performing meditation or exercise session with other subjects or in a group of subjects. The personalized cue that may include, but is not limited to, a plug-in port for inserting a headset or a wireless connection to a headset, a viewing screen on a cue generation device or a smartphone and a haptic sensing or tactile feedback option embedded in the cue generation unit 130 etc.

In an exemplary embodiment of the present invention, the cue generation unit 130 upon receiving the modified breathing rate from the feedback unit 222 is configured to provide the modified breathing rate in a real-time to the subject. The modified breathing rate may be provided in the form of distinct acoustic signals for inhalation or exhalation in a controlled and regulated manner that may be useful for reducing the first value. The subject may adapt to the breathing rate (second modified biomarker) provided by the cue. Further, the rate of the acoustic signals may change in real-time based on the modified breathing rate by the subject. The contactless sensor device 102 is configured to further capture physiological parameters as a consequence of the modified breathing rate. The captured physiological parameters are transmitted to the computation engine 122 via the data capturing engine 106. The computation engine 122 computes and transmits another set of breathing rate, heartbeat and HRV parameters to the feedback unit 222 for computing a new second value. Consequently, the feedback unit 222 further transmit another modified breathing rate based on the computed new second value.

Figure 10A:
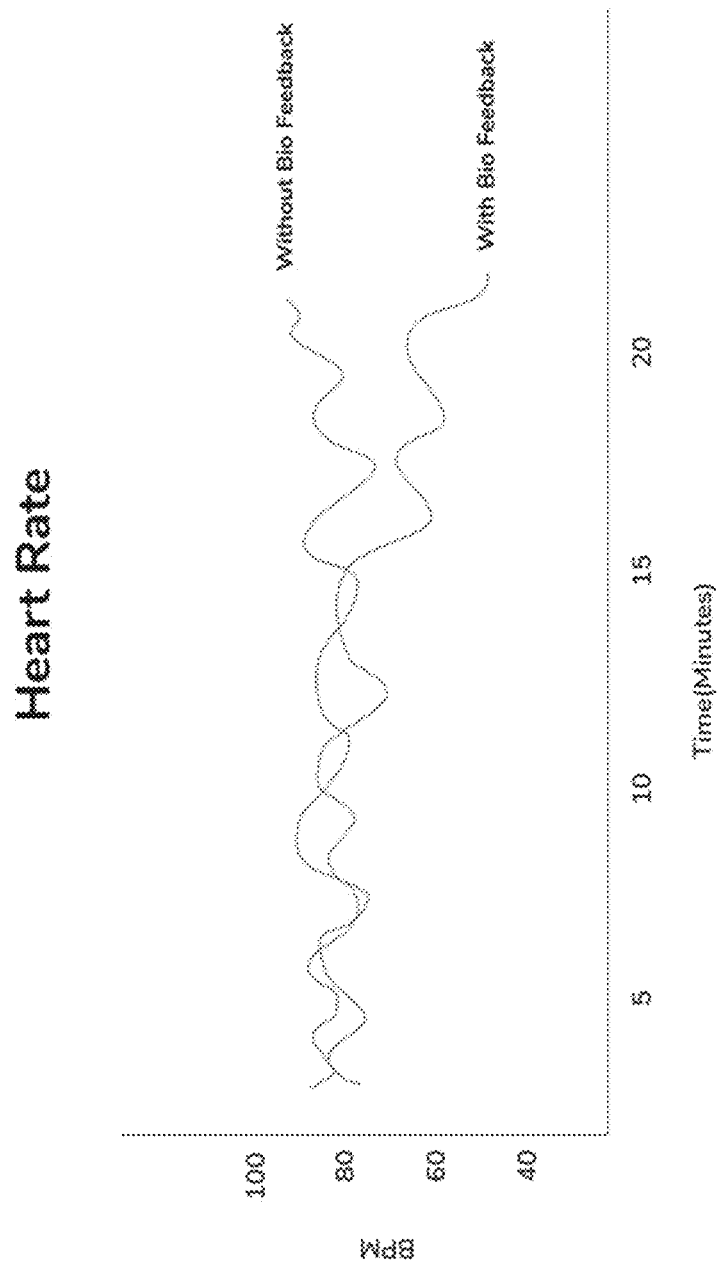
FIGS. 10a-10c illustrate a graphical representation depicting reduced heart rate, increased HRV parameter SDNN and reduced HRV parameter LF/HF depicting relaxed state with biofeedback provided to the subject, in accordance with an embodiment of the present invention, as compared to increased heart rate, reduced HRV parameter SDNN, increased HRV parameter LF/HF without the biofeedback.
Figure 10B:
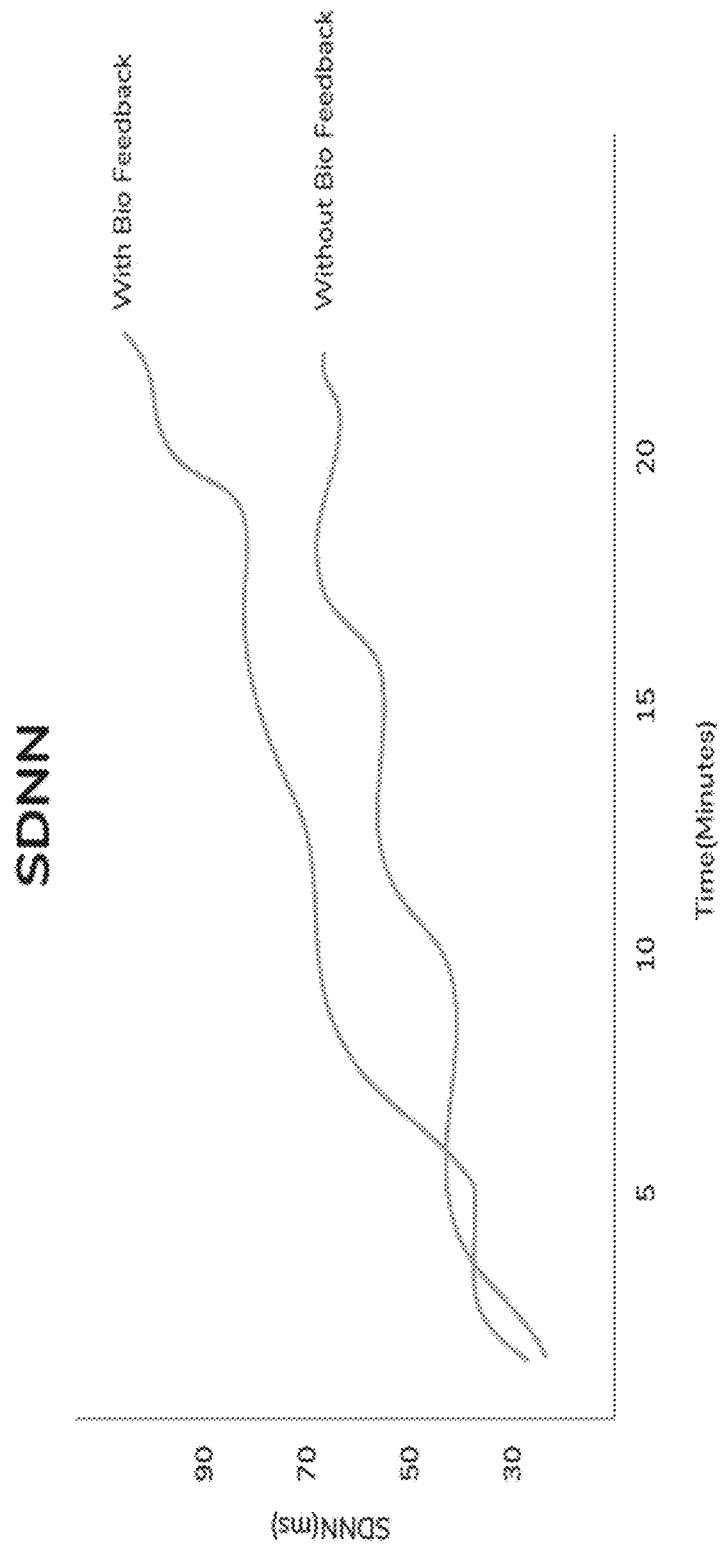
Figure 10C:
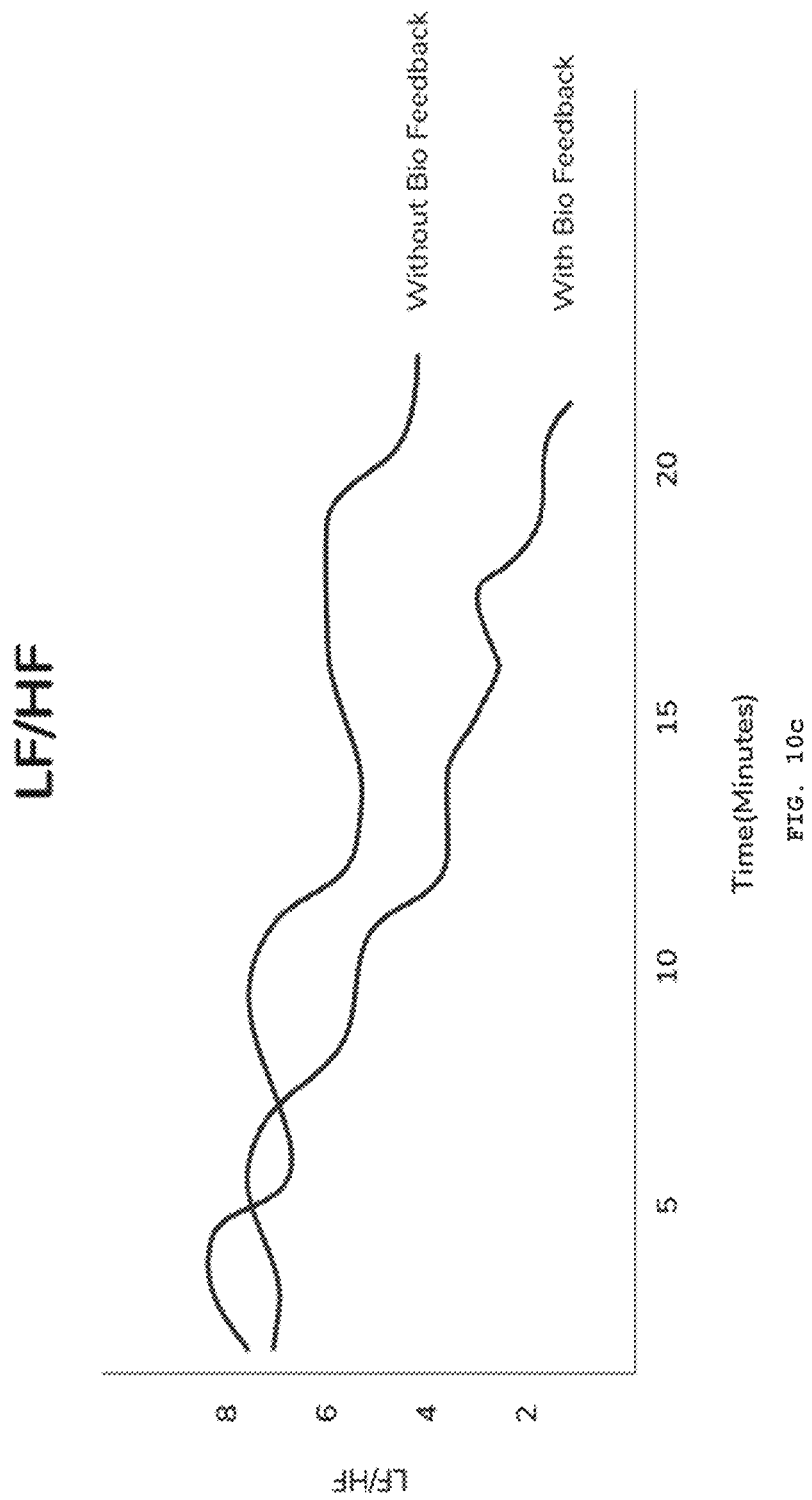
Figure 11A:
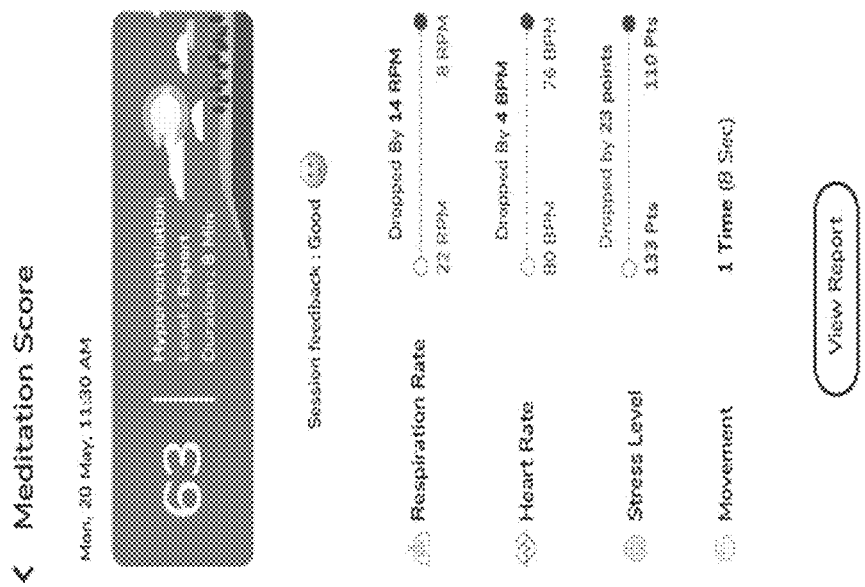
FIGS. 11a-11e illustrate screenshots, captured from a visualization unit, of detailed report of the meditation or exercise session of the subject, in accordance with an embodiment of the present invention.
Figures 11B, 11C:
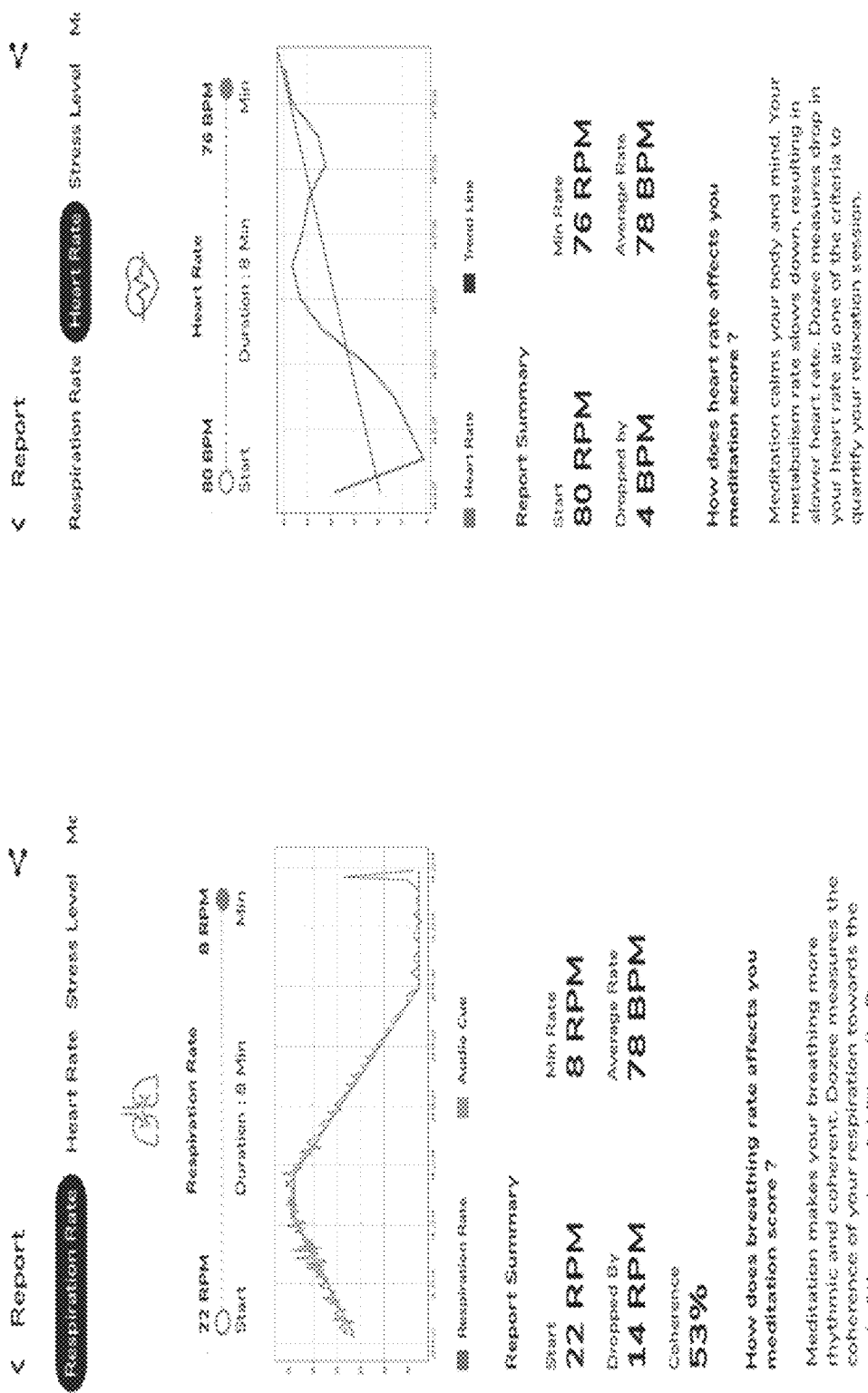
Figures 11D, 11E:
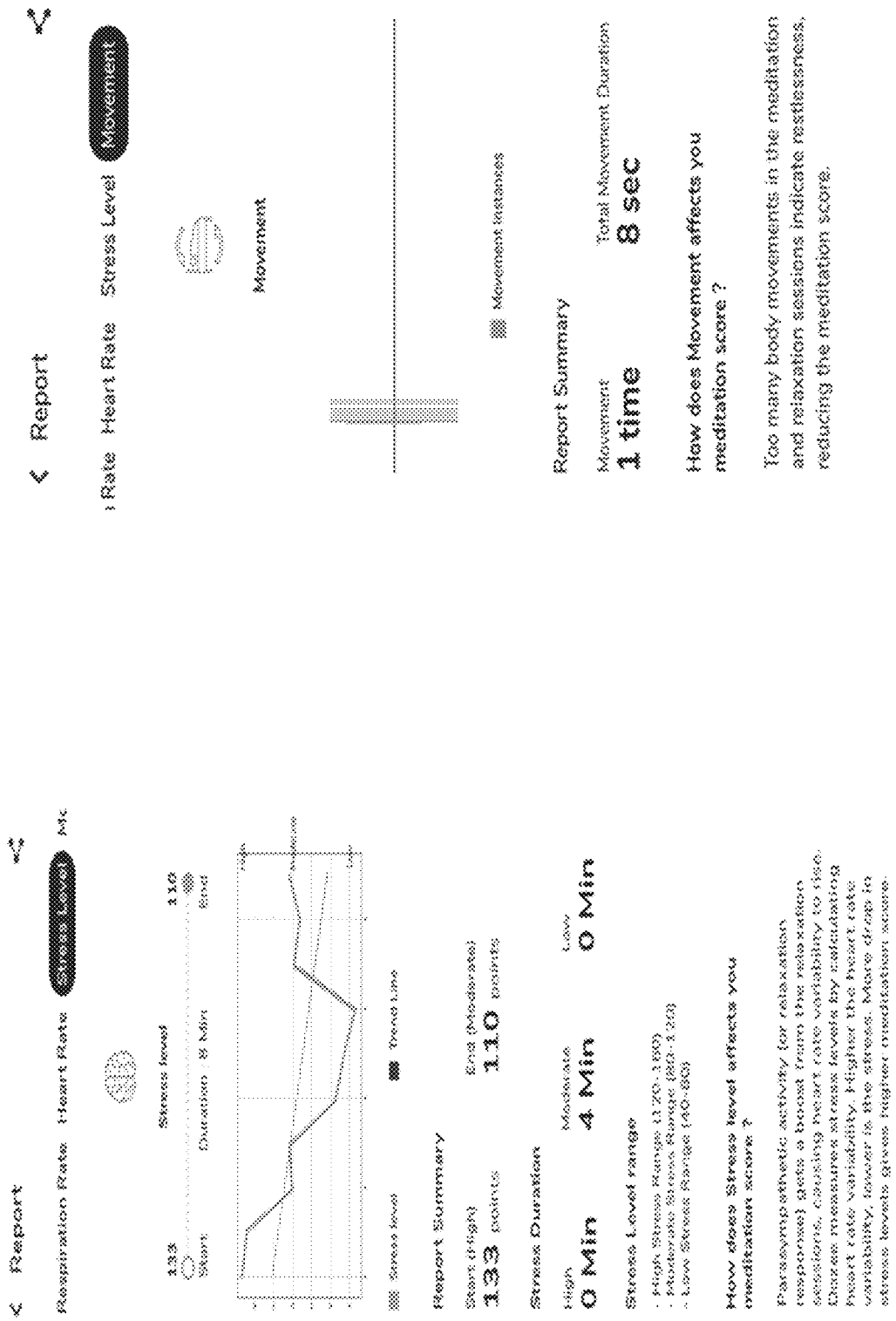

In another exemplary embodiment of the present invention, the cue generation unit 130, upon receiving the modified breathing rate from the feedback unit 222, is configured to provide the modified breathing rate in real-time to the subject in the form of haptic feedback of smartphone vibrations along with the audio cue which guides the subject to breath at certain rate and follow the cue. The subject may lie down to meditate with the sensor device 102 placed under him, or he may hold the mobile phone or place it near him for receiving haptic feedback. The subject may choose either of the haptic cue or audio cue or combination of both depending upon his requirements. The audio cue may be accompanied with vibrations produced by the smart phone. A short vibration may imply inhalation, whereas a long vibration may imply exhalation. Therefore, based on the cue provided, the breathing rate of the subject is regulated which is detected by the sensor device 102. The sensor device 102 transmits the regulated breathing rate along with other physiological parameters (biomarkers) for computation to the computation subsystem 120. The computation subsystem 120 further provides the computed physiological parameters (biomarkers) to the feedback unit 222 for computing reduced stress levels. The feedback unit 222 further provides a modified cue for guiding the subject via the cue generation unit 130 which the subject may follow for achieving deep relaxation state. The cue data provided to the user may be stored in the database 118 for future retrieval. FIGS. 10a-10c illustrate a graphical representation depicting reduced heart rate, increased HRV parameter SDNN and reduced HRV parameter LF/HF depicting relaxed state with biofeedback provided to the subject, in accordance with an embodiment of the present invention, as compared to increased heart rate, reduced HRV parameter SDNN, increased HRV parameter LF/HF without the biofeedback.

In an embodiment of the present invention, the data visualization unit 132 operating in conjunction with the database 118 is configured to provide a detailed report of the meditation or exercise session of the subject as illustrated in FIG. 11a, FIG. 11b, FIG. 11c, FIG. 11d and FIG. 11e. The data visualization unit 132 includes, but is not limited to, a smartphone application, a dashboard based web application etc. The report may comprise biomarkers computed, the cue provided to the user in real-time, the evaluated relaxed state achieved after following the cue etc. The visualization unit 132 may be accessed on, but is not limited to, a smart phone, a tablet, a computer system, a smart watch etc. The visualization unit 132 is configured to uniquely authorize each subject separately by registering and providing authorization for viewing the related meditation session report. The visualization unit 132 is further configured to provide a score which is computed and based on the levels of stress computed during the meditation or exercise session and other physiological parameters for measuring the efficiency of the meditation session. In an embodiment of the present invention, the score is computed based on the parameters, which may include, but is not limited to, number of movements in the meditation session, change in heart rate, correlation of breathing rate with the breathing cue, coherence in the breathing, change in breathing rate, change in stress levels calculated utilizing HRV parameters, total time of meditation to the actual time of meditation and feedback from the subject with regard to the meditation session.

Figure 12:
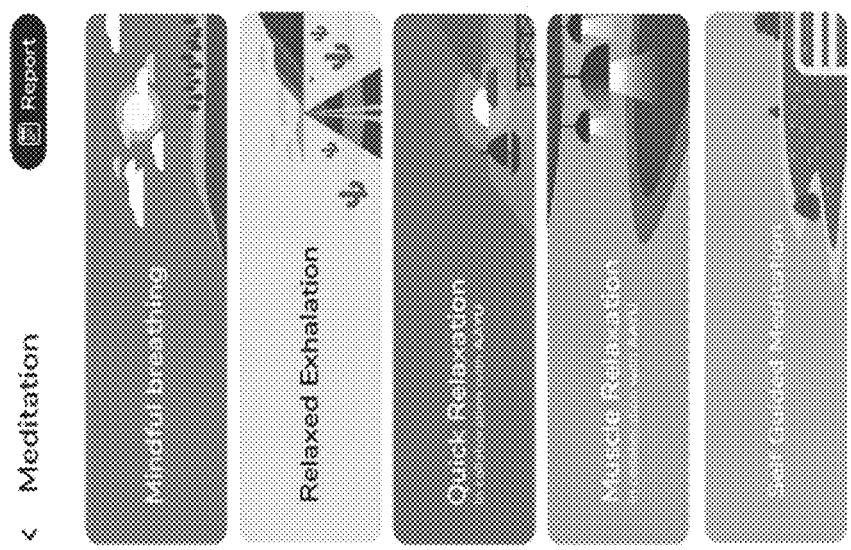
FIG. 12 illustrates a screenshot of a graphical user interface (GUI), captured from a visualization unit, depicting various types of customizable meditation session options, in accordance with an embodiment of the present invention.

In an exemplary embodiment of the present invention, the visualization unit 132 may provide a graphical user interface (GUI) to the registered and authorized subject. The GUI allows the subject to access the meditation or exercise session reports, scores etc. that may be stored in the database 118 in a pre-defined storage technique. The GUI further provides various options to the subject for selecting various types of customizable meditation session options such as, but is not limited to, hyperventilation, quick relaxation, deep relaxation etc. which the subject may select on the GUI accordingly as illustrated in FIG. 12. Further, the different types of meditations may comprise different meditation levels, background music etc. which the subject may choose on the GUI for achieving the desired relaxation state. Further, the subject may provide a feedback of the meditation or exercise session, which is stored in the database 118 along with the session reports.

Advantageously, in accordance with various embodiments of the present invention, the system 100 is configured to efficiently detect, monitor and regulate physiological parameters associated with the subject in a contactless manner and in real-time, which is agnostic of the medium type between the subject and the sensor device 102, subject's posture etc. The system 100 provides a self-learning built-in-intelligent mechanism, which does not require any prior training, for computing the physiological parameters in real-time. The system 100 is configured to appropriately capture the BCG signals associated with a subject in an unobtrusive manner. Further, the system 100 provides an effective way of quantifying a meditation or exercise session by accurately scoring the measured physiological parameters. The system 100 is, further, capable of providing the biofeedback in real-time based on the physiological parameters for providing an efficient meditation or exercise session thereby aiding in achieving a balanced autonomic nervous system. The system 100 further provides a real-time modifiable, adjustable and customized cue (biofeedback) to the subject based on the detected physiological parameters. Further, the system 100 provides a feedback system which interacts with the subject and takes inputs from the subject in real-time for efficiently improving the meditation session and aids the subject in achieving a relaxation state. Further, the system 100 provides measurement of the physiological parameters associated with the subject without disturbing or exhausting the subject. Furthermore, the system 100 is easily available, easily operable, portable, scalable and cost effective.

Figure 13:
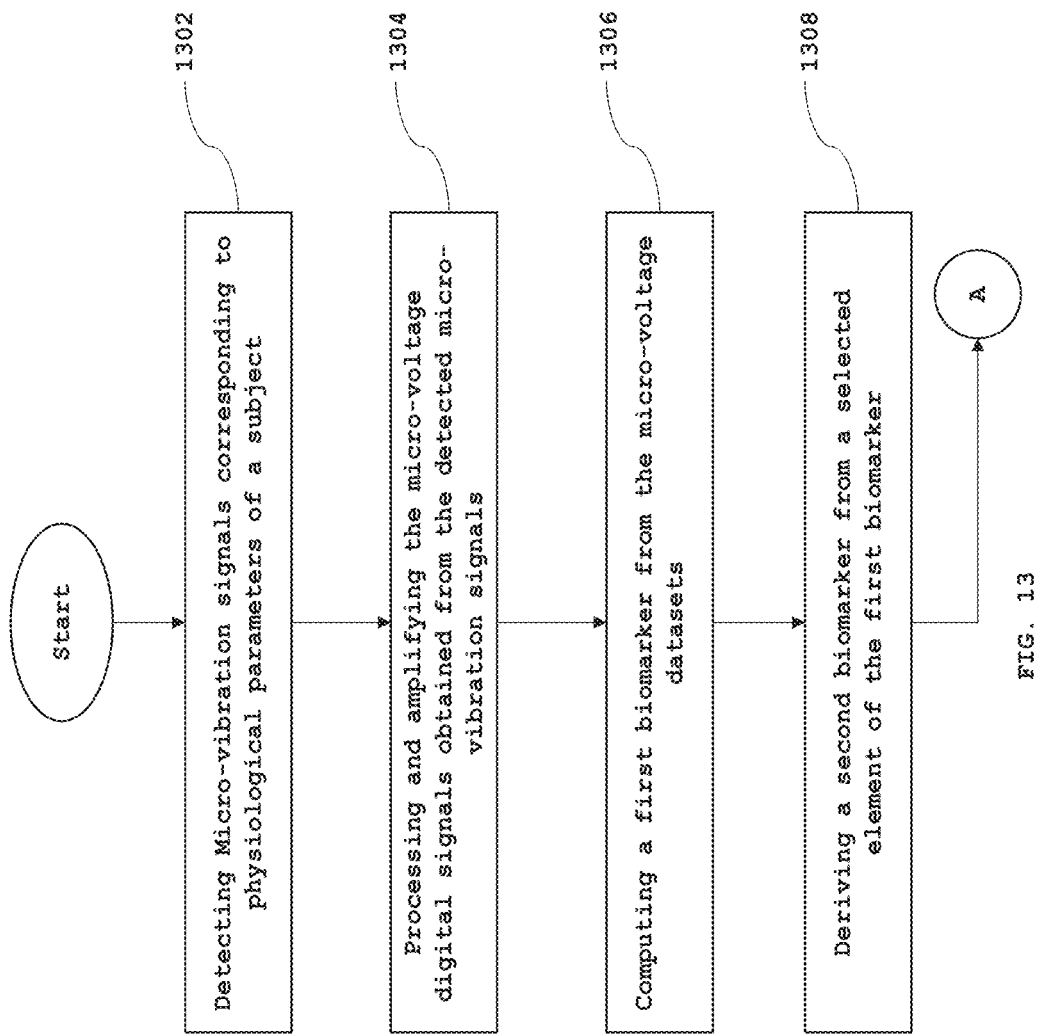

FIG. 13 is a flowchart illustrating a method for determining breathing rate as a biofeedback, in accordance with various embodiments of the present invention.

At step 1302, micro-vibration signals corresponding to physiological parameters of a subject are detected. In an embodiment of the present invention, in operation, the micro-vibrations corresponding to physiological parameters of the subject, who is in a state of meditation or exercise, are detected and captured as analog data signals in a contactless manner. The captured micro-vibrations are received through a medium placed between the subject and sensor device. For example, the micro-vibrations may be captured through a medium ranging from a thin surface such as a yoga mat to a thick surface such as a 20-inch mattress. The micro-vibrations captured include, but are not limited to, ballistocardiographic (BCG) signals associated with physiological parameters of the subject such as, breathing rates, heart rates, heart movements, chest movements, cardiac frequency etc. which may represent the state of the subject at the time of meditation or exercise. The captured micro-vibrations, which are analog signals, are converted into micro-voltage digital signals. The micro-voltage digital signals may be in the range of between 0-3.3 V.

At step 1304, the micro-voltage digital signals obtained from the detected micro-vibration signals are processed and amplified. In an embodiment of the present invention, the micro-voltage digital signals are recorded in a pre-defined data recording format at the subject's location. The pre-defined data recording format may include, but is not limited to, a chronological order.

In an embodiment of the present invention, the micro-voltage digital signal is amplified for maximizing the resolution of the micro-voltage digital signal, as desired, to accurately process the micro-voltage digital signal for efficient detection of subject's physiological parameters. The maximization of resolution of the micro-voltage digital signal is carried out without data loss or information loss that may occur due to clipping. Further, amplification and maximization of resolution of the micro-voltage digital signal aids to operate with any thickness and construction of medium at the subject's end. Multiple amplification capabilities are provided for amplifying the micro-voltage digital signal depending upon the strength of the micro-voltage signal. In an exemplary embodiment of the present invention, the multiple amplification capabilities provide, but are not limited to, eight different amplification options that amplify the micro-voltages between the range of 15× to 2500×. The calibration and selection of the amplification option is carried out automatically based on a sensitivity shifting mechanism. The sensitivity shifting mechanism depends upon the level of strength of the micro-voltage digital signal received from the subject's end, when the subject is in a meditation or exercise state.

In an embodiment of the present invention, the amplified micro-voltage digital signal is transmitted to a database via a communication channel (not shown). The communication channel (not shown) may include, but is not limited to, a wire or a logical connection over a multiplexed medium, such as, a radio channel in telecommunications and computer networking. Examples of telecommunications and computer networking may include a local area network (LAN), a metropolitan area network (MAN), a wide area network (WAN) or any wired or wireless network, such as, but not limited to, Wi-Fi, Bluetooth® Classic, Bluetooth® Low Energy etc. In an exemplary embodiment of the present invention, the database may be positioned at the location of the sensor device and the data capturing subsystem. For example, the database may be installed on a smartphone, tablet, laptop, computer system etc. of the subject. In another exemplary embodiment of the present invention, the database may be positioned at a location remote to the sensor device and the data capturing subsystem, such as, in a cloud based server. In an embodiment of the present invention, the database is configured to store the micro-voltage digital signal in a pre-defined data storage format which may include, but not limited to, one or more datasets in a chronological order.

At step 1306, a first biomarker is computed from the micro-voltage datasets. In an embodiment of the present invention, a set of pre-defined rules are applied for processing the micro-voltage datasets corresponding to the physiological parameters related to one or more subjects. The set of pre-defined rules are based on various empirical studies of physiological parameter data collected from prior experimentation, physiological parameter data collected from various subjects and data collected based on learning pattern developed over a period of time. In various embodiments of the present invention, the set of pre-defined rules may be updated from time to time. The set of rules are applied for effective analysis, processing and identification of physiological parameter.

In operation, in an embodiment of the present invention, the stored micro-voltage datasets are received from the database and subsequently a first set of rules are applied on micro-voltage datasets for extracting a first biomarker and select an element from the first biomarker. The first biomarker represents a 'body movements' element, a 'no body movements' element and a 'body artifacts' element corresponding to the subjects. In an exemplary embodiment of the present invention, the first biomarker is extracted by processing the micro-voltage dataset to obtain multiple dataset points which are individual points in an n-dimensional space. The unsupervised cognitive techniques such as, but not limited to, density based spatial clustering of applications with noise (DBSCAN) technique etc. are applied for clustering similar dataset points in the n-dimensional space to identify the first biomarker and selecting the 'no body movements' element. In an exemplary embodiment of the present invention, the similar dataset points are clustered by calculating a Euclidean distance and further calculating a standard deviation between each point in the search space. In an exemplary embodiment of the present invention, the dataset points clustered may be classified as 'body movements' element, 'no body movements' element and 'body artifacts' element for appropriately categorizing the subject's body movements. The 'body movements' element and 'body artifacts' element may include, but are not limited to, unwanted body movements, twitches, external mechanical or electrical noises etc. The clusters relating to 'body movements' element and the 'body artifacts' element are removed and isolated from the physiological parameter datasets after clustering, thereby selecting the 'no body movement' element. The 'no body movements' element is selected for determining physiological parameters, which otherwise would not have been distinguishable due to 'body movements' element and 'body artifacts' element.

At step 1308, a second biomarker is derived from a selected element of the first biomarker. In an embodiment of the present invention, 'the no body movements' element is further processed by a digital signal processing filter, such as, but is not limited to, a Butterworth filter for filtering and extracting the second biomarker utilizing a second set of rules from pre-defined set of rules. The second biomarker represents respiratory signal extracted from the selected 'no body movement' element. The second biomarker may also relate to breathing rate of the subject. The respiration signal may be extracted in the form of a sinusoidal wave which may comprise some noise elements. Therefore, the second biomarker representing the respiratory signal is in the form of the sinusoidal wave. Further, the noise element present in the sinusoidal wave is removed and subsequently an output comprising a uniform sinusoidal wave representing the breathing cycles as respiratory signal is provided. The sinusoidal wave representing the respiratory signal is processed for extracting and computing each breathing cycle associated with the subject. The breathing cycles are extracted and computed based on total number of maximas and minimas present in the sinusoidal wave. The maximas and minimas of the sinusoidal wave are extracted separately into multiple template forms. In an exemplary embodiment of the present invention, all the extremas of the sinusoidal signal are computed and some points before and after the extrema points are taken to form the template. The extracted templates may comprise either maxima or minima of the sinusoidal wave form representing breathing cycles. In an exemplary embodiment of the present invention, the unsupervised machine learning based techniques such as, but not limited to, data clustering techniques are applied on the extracted and formed templates. The templates comprising similar patterns i.e. either maxima or minima are clustered together in one cluster. Similar template clusters are therefore formed comprising either maxima or minima associated with the breathing cycles. In an exemplary embodiment of the present invention, the formed templates are segregated, preferably, into three clusters for adequately determining the breathing cycles based on clustering techniques such as, but is not limited to, K-means++ clustering. In an exemplary embodiment of the present invention, the templates are segregated into three clusters by computing Euclidean distances between the templates. Further, out of the three template clusters, a first principal template is selected from the formed clusters. The first principal template is representative of maximum number of breathing instances or respiration cycles. The first principal template is selected based on the Euclidean distance of cluster centers with respect to each other. In particular, the template cluster farthest from the other two template clusters is selected as the first principal template.

At step 1310, a third biomarker is derived from a selected element of the first biomarker. In an embodiment of the present invention, the 'no body movements' element are further processed for subsequent filtering and extracting a third biomarker by applying a third set of rules, from the pre-defined set of rules. The third biomarker is representative of a heartbeat or cardiac signal dataset in the form of a waveform. The heartbeat or cardiac signal dataset waveforms are representative of heartbeats that may occur when the subject is in a meditation or exercise state. Each heartbeat from the cardiac signals is extracted in the form of multiple heart beat signal waveforms. The third set of rules are further applied for appropriately transmitting the multiple heartbeat signal waveforms for processing. The multiple heartbeat signal waveforms are processed and analyzed for forming multiple templates corresponding to multiple heartbeat signal waveforms. In an exemplary embodiment of the present invention, the signal between three continuous maximas and two continuous minimas are processed to form the heartbeat waveform signal template. The templates are processed and analyzed for assessing similarity between the heartbeat signal templates by applying unsupervised machine learning techniques such as, but is not limited to, clustering techniques for clustering the similar templates. In an exemplary embodiment of the present invention, the formed templates are clustered, preferably, into eight clusters based on the Euclidean distance technique. Further, a second principal template is selected from the formed eight template clusters based on the frequency composition of the centroid template. The second principal template is representative of a template cluster having a maximum number of heartbeats. In an exemplary embodiment of the present invention, the second principal template may further be selected based on a frequency analysis technique, a Fast Fourier Transform (FFT) technique etc. The second principal template may comprise highest power in a desired frequency range.

In an embodiment of the present invention, one or more extracted heartbeats in the template form may be clustered in a different cluster other than the clusters utilized for selecting the second principal template. The clustered heartbeat waveform signal templates are analyzed for identifying potential instances of missing heartbeats by analyzing abnormal intervals between neighboring heartbeats determined based on the second principal template. In an exemplary embodiment of the present invention, the identification of missing heartbeats is carried out based on correlation assessment techniques such as, but is not limited to, a Pearson correlation technique. Consequently, the missing heartbeats from the second principal template are also detected and clustered appropriately. In an exemplary embodiment of the present invention, an abnormal interval in the clustering of the heartbeat templates is detected if the time interval between two successive heartbeats is found to be considerably more than the average time interval between the successive heartbeats for a pre-determined period. The templates in that interval are then compared to the centroid of the selected cluster and the Pearson correlation coefficient is computed. Thereafter, if any template has significant Pearson correlation coefficient, it is selected as a heartbeat.

At step 1312, a fourth biomarker is computed based on the third biomarker. In an embodiment of the present invention, each individual heartbeat which is detected based on the second principal template is computed for determining the fourth biomarker. The fourth biomarker is representative of the heart rate variability (HRV) parameters associated with the heartbeats. The HRV parameters are representative of variation in the time interval between each heartbeat. The detection of HRV parameters aids in determining the state of autonomic nervous system (ANS) of the subject for effectively determining and evaluating stress levels of the subject at the beginning of meditation or exercise session until the end of the session. Therefore, in order to measure HRV parameters (fourth biomarker), variation in the beat to beat time intervals is computed. In particular, the HRV parameters are computed by computing time and frequency domain parameters related to each heartbeat interval. The time domain parameters computed may include, but are not limited to, standard deviation of normal-to-normal intervals (SDNN), standard deviation of the average normal-to-normal intervals (SDANN), root mean square of successive differences (RMSSD) and proportion of NN50 (pNN50). Further, the frequency domain parameters computed may include, but is not limited to, very low frequency (VLF), low frequency (LF), high frequency (HF) and ratio of LF to HF (LF/HF). Firstly, time domain parameters are determined by providing a timestamp for each heartbeat interval and subsequently the frequency domain parameters are determined. In an exemplary embodiments of the present invention, firstly the time domain parameters associated with heartbeats are computed. Then, the SDNN and SDANN parameters associated with a heartbeat are determined. SDNN is computed by determining standard deviation of NN intervals for every 30 seconds. Further, SDANN is computed as standard deviation of the average NN intervals calculated for over short intervals of time period, preferably, for 5 minutes. SDNN further provides all the cyclic components responsible for variability in the period of recording, and therefore it represents the total variability. Further, RMSSD is computed by calculating the square root of the mean of the squares of the successive differences between adjacent NNs.

Subsequently, pNN50 is computed by calculating the proportion of NN50 divided by total numbers of NNs. NN50 count, therefore, is the mean number of times per hour in which the change in consecutive normal (NN) intervals exceeds 50 milliseconds. Further, after computing time domain parameters, frequency domain parameters are computed. Bands of frequency are assigned and subsequently the number of NN intervals that match each band is determined. The frequency bands may comprise high frequency (HF) in the range of 0.15 to 0.4 Hz, low frequency (LF) in the range of 0.04 to 0.15 Hz and very low frequency (VLF) in the range of 0.0033 to 0.04 Hz. Further, after assigning the frequency bands, the frequency bands are analyzed for determining the frequency domain parameters. In an exemplary embodiment of the present invention, the frequency bands are analyzed based on a parametric power spectral density (PSD) and non-parametric PSD for determining power distribution across frequencies. In another exemplary embodiment of the present invention, frequency parameters are computed based on techniques such as, but are not limited to, Fast Fourier Transform (FFT) and Lomb-Scargle (LS) periodogram. In an embodiment of the present invention, the extracted first, second, third and fourth biomarkers are stored in the database. The stored data is capable of being retrieved for viewing by the subject.

At step 1314, a first value is computed based on the second, third and fourth biomarker. At step 1316, a second value is computed based on the first value. In an embodiment of the present invention, the second, third and fourth biomarker are representative of breathing rates of the subject, heart rate of the subject and HRV parameters associated with the heartbeat. In various embodiments of the present invention, the breathing rate which is in control of the subject is regulated by computing a second value from a first value which is computed as a function of second, third and fourth biomarker. The first value is indicative of stress levels of the subject. The second value is indicative of a reduced stress level of the subject. Therefore, the meditation or exercise session is optimized based on guidance provided in the form of regulated breathing rate, to which the subject may adapt for achieving the most relaxed and stress free state.

In particular, in order to optimize the meditation or exercise session, the first value associated with each of the biomarkers are computed. In an exemplary embodiment of the present invention, the computation of the first value is carried out by computing stress as a function of second, third and fourth biomarkers that represents, breathing rate, heart rate and HRV parameters. In one example, the first value is computed as a non-linear function of breathing rate, heart rate and time domain HRV parameters and frequency domain HRV parameters.

In an embodiment of the present invention, the second value computed by regulating the computed first value. In an exemplary embodiment of the present invention, a correlation is determined between the first value and a time domain parameter of the fourth biomarker and a frequency domain parameter of the fourth biomarker for computing a second value. In an exemplary embodiment of the present invention, the correlation is representative of an inverse relationship between the first value and the time domain parameter of the fourth biomarker and a direct relationship between the first value and the frequency domain parameter of the fourth biomarker. In particular, the first value is inversely proportional to SDNN, RMSSD, pNN50 and HF parameters associated with the HRV parameters and directly proportional to the LF and LF/HF parameters associated with the HRV parameters. The second value is computed by maximizing the SDNN parameter associated with the time domain HRV parameter (fourth biomarker) and minimizing LF/HF parameter associated with the frequency domain HRV parameter (fourth biomarker). Therefore, by maximizing SDNN parameter and minimizing LF/HF parameter, the first value associated with the subject reduces and the reduced value is the second value. In exemplary embodiment of the present invention, a regression model based technique with back propagation is utilized for optimizing the meditation or exercise session by adequately computing the second value.

At step 1318, a biofeedback is provided as a cue. In an embodiment of the present invention, a biofeedback, in real-time is transmitted to the cue generation unit. The biofeedback is representative of a quantified data that is determined based on the second value. The quantified data is indicative of a modified second biomarker i.e. breathing rate obtained based on the computed second value. In an exemplary embodiment of the present invention, the breathing rate is modified in every 5-10 seconds. The modified breathing rate aids the subject in achieving a relaxed state.

In another embodiment of the present invention, the modified breathing rate is communicated to the subject as a cue in real-time during the meditation or exercise session. Further, a modified breathing rate is provided, since the breathing rate is in control of the subject. Therefore, by providing a modified breathing rate to the subject as biofeedback, the dependent physiological levels such as heart rate and heart rate variability (HRV) parameters are also controlled. The modified breathing rate is provided to the subject as a cue in the form of, but is not limited to, an audio, a video and haptic feedback.

In an embodiment of the present invention, the subject performing meditation or exercise may be able to view, listen, sense or feel the generated cue. Further, the subject performing the meditation or exercise may be able to get a personalized cue. The cue may be viewed, listened, sensed or felt by that subject. The personalized cue is provided to the subject, if subject is performing meditation or exercise session with other subjects or in a group of subjects. The personalized cue may include, but is not limited to, a plug-in port for inserting a headset or a wireless connection to a headset, a viewing screen on a cue generation device or a smartphone and a haptic sensing or tactile feedback option etc.

In an exemplary embodiment of the present invention, the modified breathing rate may be provided in a real-time to the subject. The modified breathing rate may be provided in the form of distinct acoustic signals for inhalation or exhalation in a controlled and regulated manner that may be useful for reducing the stress levels. The subject may adopt the breathing rate (second modified biomarker) provided by the cue. Further, the rate of the acoustic signals may change in real-time based on the modified breathing rate by the subject. Physiological parameters are captured as a consequence of the modified breathing rate and another set of breathing rate, heartbeat and HRV parameters are computed for a new second value and an another modified breathing rate is provided based on the computed new second value.

In another exemplary embodiment of the present invention, a modified breathing rate is provided, in real-time, to the subject in the form of haptic feedback of smartphone vibrations along with the audio cue which guides the subject to breath at certain rate and follow the cue. The subject may lie down to meditate with the sensor device placed under him, or he may hold the mobile phone or place it near him for receiving haptic feedback. The subject may choose either of the haptic cue or audio cue or combination of both depending upon his requirements. The audio cue may be accompanied with vibrations produced by the smart phone. A short vibration may imply inhalation, whereas a long vibration may imply exhalation. Therefore, based on the cue provided, the breathing rate of the subject is regulated which may be detected by the sensor device. Further, the regulated breathing rate along with other physiological parameters (biomarkers) are computed for reducing stress levels. Further, a modified cue may be provided for guiding the subject which the subject may follow for achieving deep relaxation state. The cue data provided to the user may be stored in the database for future retrieval. Therefore, the subject adapting to the cue achieve regulated physiological parameters with reduced levels of stress and a more relaxed state.

In an embodiment of the present invention, a detailed report of the meditation or exercise session of the subject is provided. The report may be viewed via, but is not limited to, a smartphone application, a dashboard based web application etc. The report may comprise biomarkers computed, the cue provided to the user in real-time, the evaluated relaxed state achieved after following the cue etc. The report may be accessed on, but not limited to, a smart phone, a tablet, a computer system, a smart watch etc. Each subject is uniquely authorized separately by registering and providing authorization for viewing the related meditation session report. Further, a score is provided, computed and based on the levels of stress computed during the meditation or exercise session for measuring the efficiency of the meditation session. In an embodiment of the present invention, the score is computed based on the parameters, which may include, but is not limited to, number of movements in the meditation session, change in heart rate, correlation of breathing rate with the breathing cue, coherence in the breathing, change in breathing rate, change in stress levels calculated utilizing HRV parameters, total time of meditation to the actual time of meditation and feedback from the subject with regard to the meditation session.

In an exemplary embodiment of the present invention, a graphical user interface (GUI) is provided to the registered and authorized subject. The GUI allows the subject to access the meditation or exercise session reports, scores etc. that may be stored in the database in a pre-defined storage technique. The GUI further provides various options to the subject for selecting various types of customizable meditation session options such as, but is not limited to, hyperventilation, quick relaxation, deep relaxation etc. which the subject may select on the GUI accordingly. Further, the different types of meditations may comprise different types of meditation levels, background music etc. which the subject may choose on the GUI for achieving the desired relaxation state. Furthermore, the subject may provide a feedback of the meditation or exercise session, which is stored in the database along with the session reports. The GUI is configured to further provide a comparison, via a graphical representation, between the meditation session with the biofeedback and without the biofeedback during the meditation or exercise session.

Figure 14:
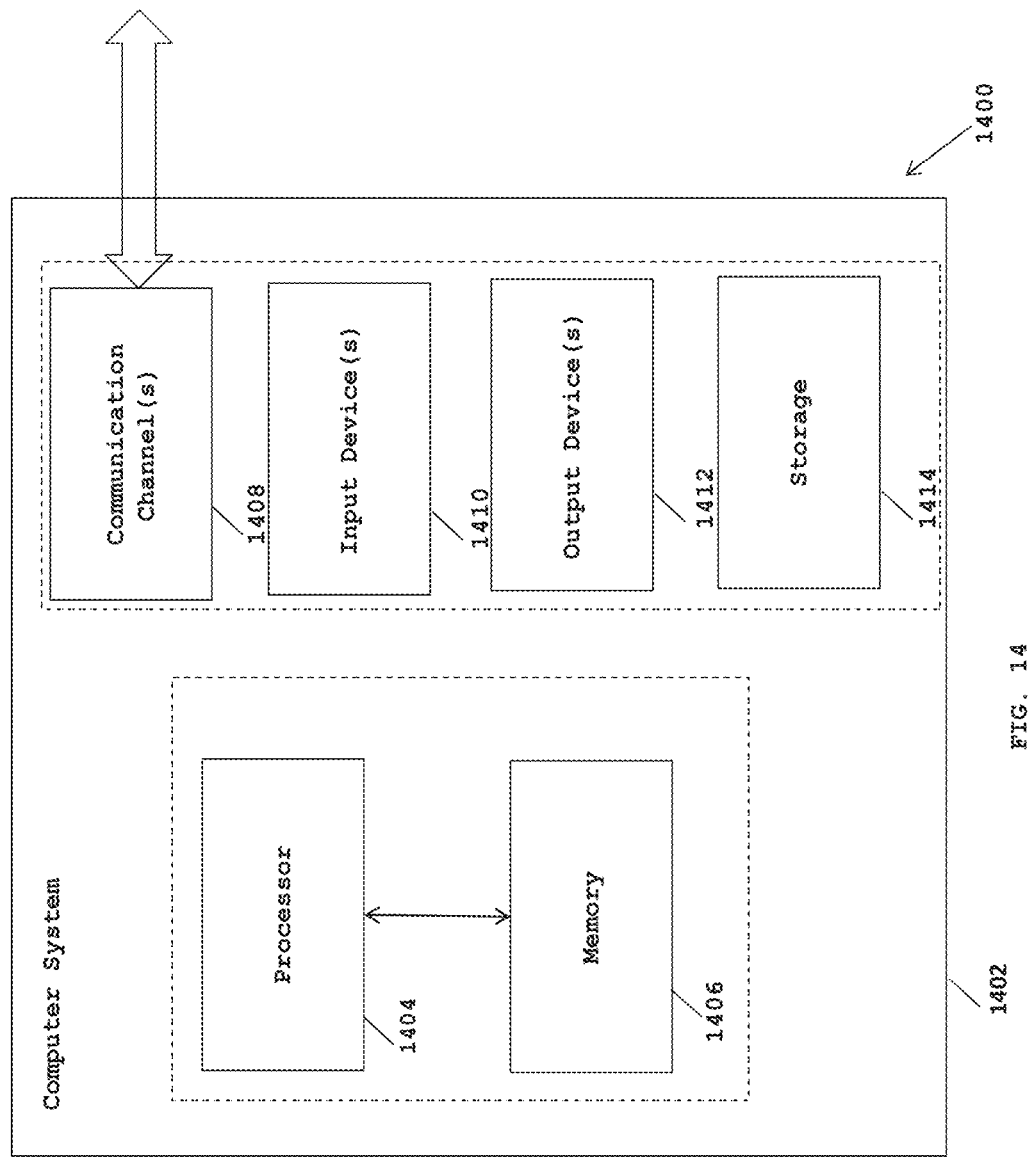
FIG. 14 illustrates an exemplary computer system in which various embodiments of the present invention may be implemented.

FIG. 14 illustrates an exemplary system 1400 in which various embodiments of the present invention may be implemented. The computer system 1402 comprises a processor 1404 and a memory 1406. The processor 1404 executes program instructions and is a real processor. The computer system 1402 is not intended to suggest any limitation as to scope of use or functionality of described embodiments. For example, the computer system 1402 may include, but is not limited to, a programmed microprocessor, a micro-controller, a peripheral integrated circuit element, and other devices or arrangements of devices that are capable of implementing the steps that constitute the method of the present invention. In an embodiment of the present invention, the memory 1406 may store software for implementing various embodiments of the present invention. The computer system 1402 may have additional components. For example, the computer system 1402 includes one or more communication channels 1408, one or more input devices 1410, one or more output devices 1412, and storage 1414. An interconnection mechanism (not shown) such as a bus, controller, or network, interconnects the components of the computer system 1402. In various embodiments of the present invention, operating system software (not shown) provides an operating environment for various softwares executing in the computer system 1402, and manages different functionalities of the components of the computer system 1402.

The communication channel(s) 1408 allow communication over a communication medium to various other computing entities. The communication medium provides information such as program instructions, or other data in a communication media. The communication media includes, but not limited to, wired or wireless methodologies implemented with an electrical, optical, RF, infrared, acoustic, microwave, Bluetooth® or other transmission media.

The input device(s) 1410 may include, but not limited to, a keyboard, mouse, pen, joystick, trackball, a voice device, a scanning device, touch screen or any another device that is capable of providing input to the computer system 1402. In an embodiment of the present invention, the input device(s) 1410 may be a sound card or similar device that accepts audio input in analog or digital form. The output device(s) 1412 may include, but not limited to, a user interface on CRT or LCD, printer, speaker, CD/DVD writer, or any other device that provides output from the computer system 1402.

The storage 1414 may include, but not limited to, magnetic disks, magnetic tapes, CD-ROMs, CD-RWs, DVDs, flash drives or any other medium which can be used to store information and can be accessed by the computer system 1402. In various embodiments of the present invention, the storage 1414 contains program instructions for implementing the described embodiments.

The present invention may suitably be embodied as a computer program product for use with the computer system 1402. The method described herein is typically implemented as a computer program product, comprising a set of program instructions which is executed by the computer system 1402 or any other similar device. The set of program instructions may be a series of computer readable codes stored on a tangible medium, such as a computer readable storage medium (storage 1414), for example, diskette, CD-ROM, ROM, flash drives or hard disk, or transmittable to the computer system 1402, via a modem or other interface device, over either a tangible medium, including but not limited to optical or analogue communications channel(s) 1408. The implementation of the invention as a computer program product may be in an intangible form using wireless techniques, including but not limited to microwave, infrared, Bluetooth® or other transmission techniques. These instructions can be preloaded into a system or recorded on a storage medium such as a CD-ROM, or made available for downloading over a network such as the internet or a mobile telephone network. The series of computer readable instructions may embody all or part of the functionality previously described herein.

The present invention may be implemented in numerous ways including as a system, a method, or a computer program product such as a computer readable storage medium or a computer network wherein programming instructions are communicated from a remote location.

While the exemplary embodiments of the present invention are described and illustrated herein, it will be appreciated that they are merely illustrative. It will be understood by those skilled in the art that various modifications in form and detail may be made therein without departing from or offending the spirit and scope of the invention.

We claim:

1. A system for regulating breathing rate of a subject during a meditation session or an exercise session, the system comprising:
   a memory storing program instructions; and
   a processor executing program instructions stored in the memory and configured to:
      compute a first biomarker from micro-voltage datasets corresponding to physiological parameters associated with a subject received from a contactless sensor device;
      derive a second biomarker and a third biomarker from a selected element of the first biomarker and derive a fourth biomarker from the derived third biomarker, wherein the second biomarker and the third biomarker are derived by applying machine learning clustering to extract maximas and minimas of signal waveforms into multiple templates, segregate the multiple templates into template clusters, and select a first principal template and a second principal template from the template clusters which are representative of a maximum number of instances of the second biomarker and the third biomarker respectively;
      compute a first value in real-time as a function of the derived second biomarker, the derived third biomarker, and the derived fourth biomarker, wherein the first value is indicative of a stress level of the subject;
      determine a correlation between the first value and a time domain Standard Deviation of Normal-to-Normal intervals (SDNN) parameter of the fourth biomarker and a frequency domain Low Frequency/High Frequency (LF/HF) parameter of the fourth biomarker, wherein the correlation is representative of an inverse relationship between the first value and the time domain parameter of the fourth biomarker and a direct relationship between the first value and the frequency domain parameter of the fourth biomarker;
      compute a second value by regulating the computed first value, wherein the first value is regulated by maximizing the SDNN parameter of the fourth biomarker and minimizing the LF/HF parameter of the fourth biomarker, wherein the maximization of the SDNN parameter and the minimization of the LF/HF parameter result in reduction of the first value based on the determined correlation, the reduced first value is the computed second value which is indicative of a reduced stress level of the subject; and
      transmit a biofeedback in real-time to a cue generation unit, the biofeedback is representative of a quantified data that is determined based on the second value, wherein the quantified data is indicative of a modified second biomarker for optimizing a meditation or exercise session of a subject to a relaxed and stress-free state based on a cue generated by the cue generation unit in the form of an audio, a video and a haptic feedback.

2. The system as claimed in claim 1, wherein the processor receives the physiological parameters from a database in a predetermined format.

3. The system as claimed in claim 1, wherein the processor receives the physiological parameters from the contactless sensor device and transmits the physiological parameters to a database.

4. The system as claimed in claim 3, wherein the processor records micro-voltage digital signal corresponding to the physiological parameters which are captured in the form of micro-vibrations by the contactless sensor device and stored as the micro-voltage datasets in a chronological order.

5. The system as claimed in claim 4, wherein the processor amplifies the micro-voltage digital signal for maximizing resolution of the micro-voltage digital signal, the maximizing includes amplification between the range of 15× to 2500×.

6. The system as claimed in claim 1, wherein the first biomarker represents a 'body movements' element, a 'no body movements' element and a 'body artifacts' element associated with the subject.

7. The system as claimed in claim 6, wherein the processor extracts the first biomarker from the physiological parameters associated with the subject by processing the physiological parameters as multiple dataset points and applying a Density Based Spatial Clustering of Applications with Noise (DBSCAN) technique for clustering similar dataset points to identify the first biomarker and selecting the 'no body movement' element.

8. The system as claimed in claim 7, wherein the processor derives the second biomarker from the selected 'no body movement' element, the second biomarker represents respiratory signal in the form of a sinusoidal wave.

9. The system as claimed in claim 8, wherein the processor processes the second biomarker for computing a total number of maximas and minimas present in the sinusoidal wave.

10. The system as claimed in claim 9, wherein the maximas and minimas of the sinusoidal wave are extracted separately into multiple templates.

11. The system as claimed in claim 10, wherein the processor applies K-means++ clustering for segregating the multiple templates into three template clusters.

12. The system as claimed in claim 11, wherein the processor selects the first principal template from the three template clusters based on a Euclidean distance of the cluster centers, wherein the first principal template is representative of maximum number of respiration cycles.

13. The system as claimed in claim 7, wherein the derives the third biomarker from the selected 'no body movement' element, the third biomarker represents heartbeat signal in the form of multiple waveforms.

14. The system as claimed in claim 13, wherein the processor processes the third biomarker to form multiple heartbeat signal waveform templates, wherein signal between three continuous maximas and two continuous minimas of each of the multiple heartbeat signal waveforms are processed to form the heartbeat waveform signal templates.

15. The system as claimed in claim 14, wherein the processor analyses each of the multiple heartbeat signal waveform templates to assess similarities therebetween for clustering similar templates, wherein the heartbeat waveform signal templates are clustered into eight template clusters based on a frequency composition of the centroid template, frequency analysis technique, and Fast Fourier Transform (FFT) technique.

16. The system as claimed in claim 15, wherein the processor selects a second principal template from the eight heartbeat signal waveform template clusters, wherein the second principal template is representative of maximum number of heartbeats.

17. The system as claimed in claim 15, wherein the processor analyzes the clustered heartbeat waveform signal templates based on a Pearson correlation technique to identify missing heartbeats by determining abnormal intervals between neighboring heartbeats.

18. The system as claimed in claim 16, wherein the processor computes the fourth biomarker from the second principal template associate with the third biomarker, the fourth biomarker represents heart rate variability (HRV) parameters associated with the heartbeat signal, wherein the HRV parameters are determined based on time domain parameters and frequency domain parameters associated with each heartbeat.

19. The system as claimed in claim 18, wherein the time domain HRV parameters includes standard deviation of normal-to-normal intervals (SDNN), standard deviation of the average normal-to-normal intervals (SDANN), root mean square of successive differences (RMSSD) and proportion of NN50 (pNN50); and frequency domain HRV parameters includes Very Low Frequency (VLF), Low Frequency (LF), High Frequency (HF) and ratio of LF to HF (LF/HF).

20. The system as claimed in claim 1, wherein the first value is computed as a non-linear function of the second biomarker, the third biomarker and the fourth biomarker.

21. The system as claimed in claim 1, wherein the processor receives from the contactless sensor device physiological parameters as a consequence of the modified second biomarker and computes another set of first, second, third and fourth biomarkers for deriving a new second value and transmitting another modified second biomarker.

22. A method for regulating breathing rate of a subject during a meditation session or an exercise session, the method comprising:
    computing, by a processor, a first biomarker from microvoltage datasets corresponding to physiological parameters associated with a subject received from a contactless sensor device;
    deriving a second biomarker and a third biomarker from a selected element of the first biomarker and deriving a fourth biomarker from the derived third biomarker, wherein the second biomarker and the third biomarker are processed by applying machine learning clustering to extract maximas and minimas of signal waveforms into multiple templates, segregate the multiple templates into template clusters, and select a first principal template and a second principal template from the template clusters which are representative of a maximum number of instances of the second biomarker and the third biomarker respectively;
    computing, by the processor, a first value in real-time as a function of the derived second biomarker, the derived third biomarker, and the derived fourth biomarker, wherein the first value is indicative of a stress level of the subject;
    determining, by the processor, a correlation between the first value and a time domain Standard Deviation of Normal-to-Normal intervals (SDNN) parameter of the fourth biomarker and a frequency domain Low Frequency/High Frequency (LF/HF) parameter of the fourth biomarker, wherein the correlation is representative of an inverse relationship between the first value and the time domain parameter of the fourth biomarker and a direct relationship between the first value and the frequency domain parameter of the fourth biomarker;
    computing, by the processor, a second value by regulating the computed first value, wherein the first value is regulated by maximizing the SDNN parameter of the fourth biomarker and minimizing the frequency domain LF/HF parameter of the fourth biomarker, wherein the maximization of the SDNN parameter and the minimization of the LF/HF parameter result in reduction of the first value based on the determined correlation, the reduced first value is the computed second value which is indicative of a reduced stress level of the subject; and
    transmitting, by the processor, a biofeedback in real-time to a cue generation unit, the biofeedback is representative of a quantified data that is determined based on the second value, wherein the quantified data is indicative of a modified second biomarker for optimizing a meditation or exercise session of a subject to a relaxed and stress-free state based on a cue generated by the cue generation unit in the form of an audio, a video and a haptic feedback.

23. The method as claimed in claim 22, wherein the physiological parameters are received in a pre-determined format.

24. The method as claimed in claim 22, wherein micro-vibrations corresponding to the physiological parameters are recorded in the form of micro-voltage digital signal and stored in as the micro-voltage datasets in a chronological order.

25. The method as claimed in claim 24, wherein the micro-voltage digital signal is amplified for maximizing resolution of the micro-voltage digital signal, the maximizing includes amplification between the range of 15× to 2500×.

26. The method as claimed in claim 22, wherein the first biomarker represents a 'body movements' element, a 'no body movements' element and a 'body artifacts' element associated with the subject.

27. The method as claimed in claim 26, wherein the first biomarker is extracted from the physiological parameters associated with the subject by processing the physiological parameters as multiple dataset points and applying a Density Based Spatial Clustering of Applications with Noise (DBSCAN) technique for clustering similar dataset points to identify the first biomarker and selecting the 'no body movement' element.

28. The method as claimed in claim 27, wherein the second biomarker is derived from the selected 'no body movement' element, the second biomarker represents respiratory signal in the form of a sinusoidal wave and wherein the second biomarker is transmitted to the processor.

29. The method as claimed in claim 28, wherein the second biomarker is processed for computing total number of maximas and minimas present in the sinusoidal wave.

30. The method as claimed in claim 29, wherein the maximas and minimas of the sinusoidal wave are extracted separately into multiple templates.

31. The method as claimed in claim 30, wherein K-means++ clustering is applied for segregating the multiple templates into three template clusters.

32. The method as claimed in claim 31, wherein the first principal template is selected from the three template clusters based on a Euclidean distance of the cluster centres, wherein the first principal template is representative of maximum number of respiration cycles.

33. The method as claimed in claim 27, wherein the third biomarker is derived from the selected 'no body movement' element, the third biomarker represents heartbeat signal in the form of multiple waveforms.

34. The method as claimed in claim 33, wherein the third biomarker is processed to form multiple heartbeat signal waveform templates, and wherein signal between three continuous maximas and two continuous minimas of each of the multiple heartbeat signal waveforms are processed to form the heartbeat waveform signal templates.

35. The method as claimed in claim 34, wherein each of the multiple heartbeat signal waveform templates are analyzed for assessing similarities therebetween for clustering similar templates, wherein the heartbeat waveform signal templates are clustered into eight template clusters based on a frequency composition of the centroid template, frequency analysis technique, and Fast Fourier Transform (FFT) technique.

36. The method as claimed in claim 35, wherein a second principal template is selected from the eight heartbeat signal waveform template clusters, wherein the second principal template is representative of maximum number of heartbeats.

37. The method as claimed in claim 35, wherein the clustered heartbeat waveform signal templates are analyzed based on a Pearson correlation technique to identify missing heartbeats by determining abnormal intervals between neighboring heartbeats.

38. The method as claimed in claim 36, wherein the fourth biomarker is computed from the second principal template associated with the third biomarker, the fourth biomarker represents heart rate variability (HRV) parameters associated with the heartbeat signal, wherein the HRV parameters are determined based on time domain parameters and frequency domain parameters associated with each heartbeat.

39. The method as claimed in claim 38, wherein the time domain HRV parameters includes standard deviation of normal-to-normal intervals (SDNN), standard deviation of the average normal-to-normal intervals (SDANN), root mean square of successive differences (RMSSD) and proportion of NN50 (pNN50) and frequency domain HRV parameters includes Very Low Frequency (VLF), Low Frequency (LF), High Frequency (HF) and ratio of LF to HF (LF/HF).

40. The method as claimed in claim 22, wherein the first value is computed as a non-linear function of the second biomarker, the third biomarker and the fourth biomarker.

41. The method as claimed in claim 22, wherein physiological parameters are received as a consequence of the modified second biomarker, and wherein another set of first, second, third and fourth biomarkers is computed for deriving the new second value, and another modified second biomarker is transmitted to the cue generation unit.

42. The method as claimed in claim 22, wherein a score of the meditation session or exercise session is generated based on a number of movements, change in heart rate, correlation of breathing rate with the breathing cue, coherence in breathing, change in breathing rate, change in first value computed based on HRV parameters, total time of meditation to an actual time of meditation and feedback from the subject.

* * * * *